US011972652B1

(12) United States Patent
Shipman, Jr. et al.

(10) Patent No.: US 11,972,652 B1
(45) Date of Patent: *Apr. 30, 2024

(54) SECURE CHARGING SYSTEM FOR ELECTRONIC DEVICES

(71) Applicant: Tech Friends, Inc., Jonesboro, AR (US)

(72) Inventors: Bobby L. Shipman, Jr., Jonesboro, AR (US); Bryan Taylor, Bono (AR); Jason Cochran, Jonesboro, AR (US); Joshua L. Parrish, Paragould, AR (US); Mark Haney, Jonesboro, AR (US); Bobby L. Shipman, III, Jonesboro, AR (US)

(73) Assignee: TECH FRIENDS, INC., Jonesboro, AR (US)

( * ) Notice: Subject to any disclaimer, the term of this patent is extended or adjusted under 35 U.S.C. 154(b) by 948 days.

This patent is subject to a terminal disclaimer.

(21) Appl. No.: 16/897,105

(22) Filed: Jun. 9, 2020

Related U.S. Application Data

(63) Continuation-in-part of application No. 16/033,045, filed on Jul. 11, 2018, now Pat. No. 10,678,302,
(Continued)

(51) Int. Cl.
*H02J 7/00* (2006.01)
*A61L 2/10* (2006.01)
(Continued)

(52) U.S. Cl.
CPC ............ *G07C 9/00658* (2013.01); *A61L 2/10* (2013.01); *A61L 2/22* (2013.01); *A61L 2/26* (2013.01);
(Continued)

(58) Field of Classification Search
CPC ........ G07C 9/00658; G07C 9/38; G07C 9/32; G07C 9/00174; A61L 2/10; A61L 2/22;
(Continued)

(56) References Cited

U.S. PATENT DOCUMENTS

| 8,498,937 B1 * | 7/2013 | Shipman, Jr. ........ G06Q 20/405 705/41 |
| 2005/0104555 A1 * | 5/2005 | Simmonds-Short .......... H02J 7/0013 340/5.1 |

(Continued)

FOREIGN PATENT DOCUMENTS

| EP | 2101390 A2 * | 9/2009 | ............ H02J 7/0027 |
| WO | WO-2012174324 A1 * | 12/2012 | .............. G07F 11/62 |

(Continued)

*Primary Examiner* — Chico A Foxx
(74) *Attorney, Agent, or Firm* — Schrantz Law Firm, PLLC; Stephen D. Schrantz

(57) ABSTRACT

The secured storage receives an electronic device including but not limited to a tablet, smart phone, mobile computing device, or other computing device. The secured storage provides a charging system that charges the device. The system selectively charges the devices based upon identified rules. The lock of the secured storage secures the electronic device within the storage. The system maintains a log of the users who access the electronic devices. The system then control access by granting access to users and restricting access to users based upon usage history, behavior, or other criteria.

6 Claims, 34 Drawing Sheets

Related U.S. Application Data which is a continuation-in-part of application No. 15/136,604, filed on Apr. 22, 2016, now Pat. No. 10,225,734, which is a continuation-in-part of application No. 14/923,271, filed on Oct. 26, 2015, now Pat. No. 10,256,645, which is a continuation-in-part of application No. 14/869,592, filed on Sep. 29, 2015, now Pat. No. 9,917,455.

(51) Int. Cl.

| | |
|---|---|
| *A61L 2/22* | (2006.01) |
| *A61L 2/26* | (2006.01) |
| *B65G 1/08* | (2006.01) |
| *B65G 15/14* | (2006.01) |
| *B65G 15/44* | (2006.01) |
| *B65G 33/06* | (2006.01) |
| *G06F 1/16* | (2006.01) |
| *G06K 7/14* | (2006.01) |
| *G07C 9/00* | (2020.01) |
| *G07C 9/32* | (2020.01) |
| *G07C 9/38* | (2020.01) |
| *G08B 21/24* | (2006.01) |
| *E05B 47/00* | (2006.01) |
| *G06Q 20/12* | (2012.01) |
| *G06Q 50/06* | (2012.01) |

(52) U.S. Cl.
CPC ......... *G06F 1/1632* (2013.01); *G06K 7/1413* (2013.01); *G07C 9/00174* (2013.01); *G07C 9/32* (2020.01); *G07C 9/38* (2020.01); *G08B 21/24* (2013.01); *H02J 7/0044* (2013.01); *A61L 2202/11* (2013.01); *A61L 2202/15* (2013.01); *A61L 2202/17* (2013.01); *E05B 47/00* (2013.01); *G06Q 20/127* (2013.01); *G06Q 50/06* (2013.01)

(58) Field of Classification Search
CPC .... A61L 2/26; A61L 2202/11; A61L 2202/15; A61L 2202/17; G06F 1/1632; G06K 7/1413; G08B 21/24; H02J 7/0044; E05B 47/00; G06Q 20/127; G06Q 50/06
See application file for complete search history.

(56) References Cited

U.S. PATENT DOCUMENTS

| | | | | |
|---|---|---|---|---|
| 2009/0278495 | A1* | 11/2009 | Kaye | H02J 7/0013 |
| | | | | 320/114 |
| 2010/0147952 | A1* | 6/2010 | Carlson | G06K 7/10752 |
| | | | | 235/462.41 |
| 2012/0078413 | A1* | 3/2012 | Baker, Jr. | G07F 17/12 |
| | | | | 700/232 |
| 2013/0252577 | A1* | 9/2013 | Jordan | H02J 7/0044 |
| | | | | 455/406 |
| 2014/0156376 | A1* | 6/2014 | Sellers | G06Q 20/3276 |
| | | | | 235/383 |
| 2014/0273929 | A1* | 9/2014 | Torgersrud | H04M 15/09 |
| | | | | 455/406 |
| 2015/0207352 | A1* | 7/2015 | Lykov | H02J 7/0013 |
| | | | | 320/107 |
| 2017/0163788 | A1* | 6/2017 | Andersen | H04N 7/142 |
| 2017/0288450 | A1* | 10/2017 | Truong | H04B 5/0037 |
| 2019/0165585 | A1* | 5/2019 | Grison | H02J 7/0044 |
| 2021/0287197 | A1* | 9/2021 | Best | G07F 17/0042 |

FOREIGN PATENT DOCUMENTS

| | | | | |
|---|---|---|---|---|
| WO | WO-2013156956 | A1 * | 10/2013 | E05G 1/08 |
| WO | WO-2019212509 | A1 * | 11/2019 | G06F 8/61 |
| WO | WO-2021188437 | A1 * | 9/2021 | G06F 21/31 |

* cited by examiner

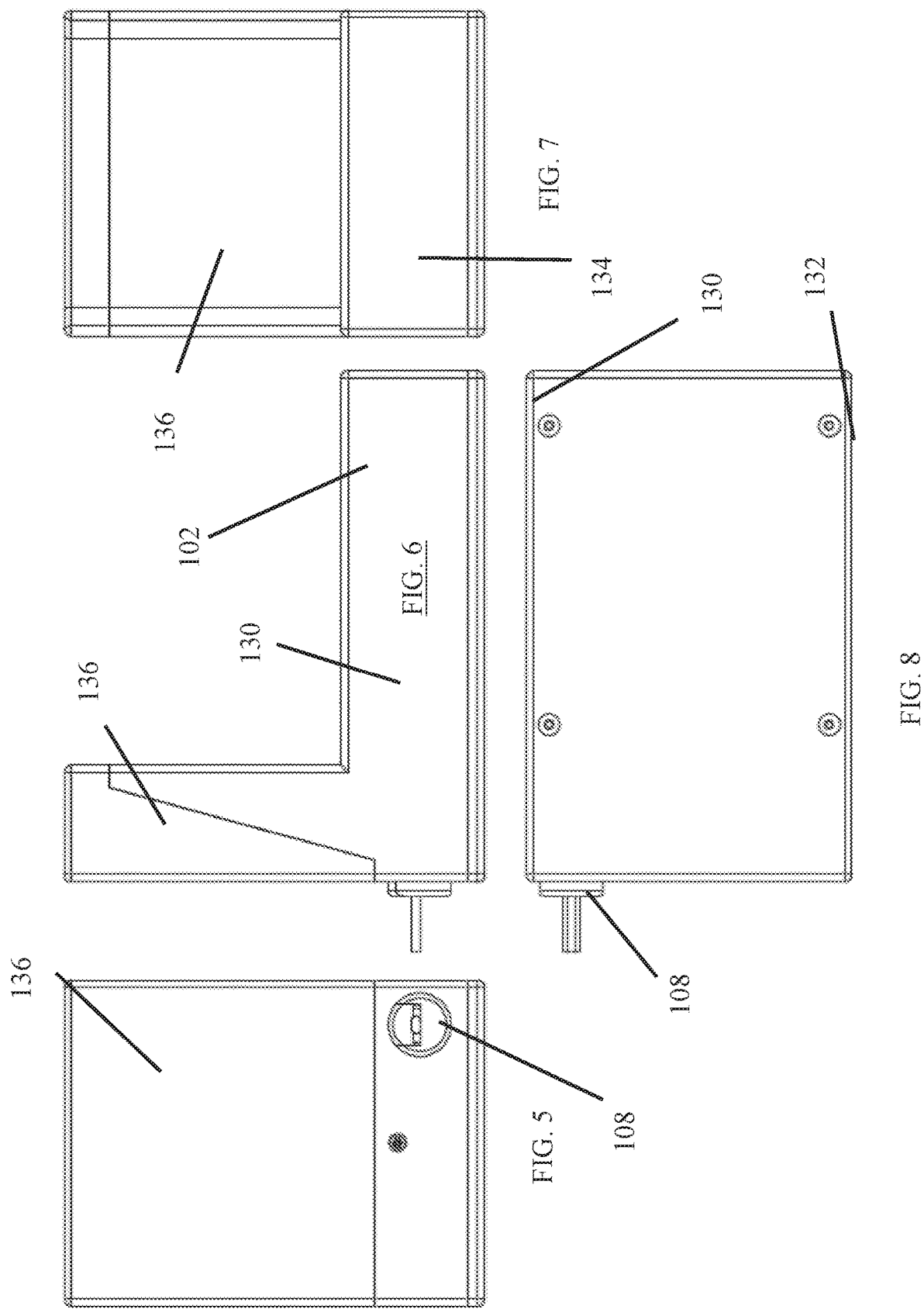

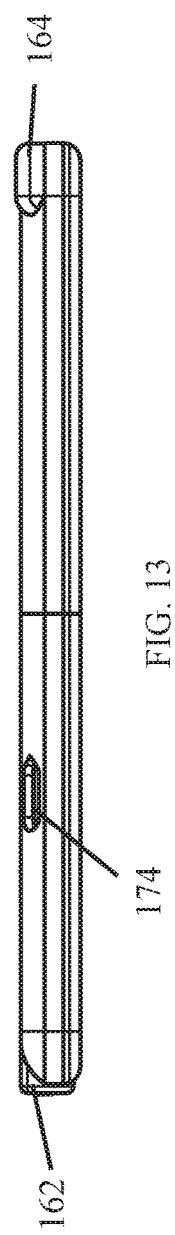
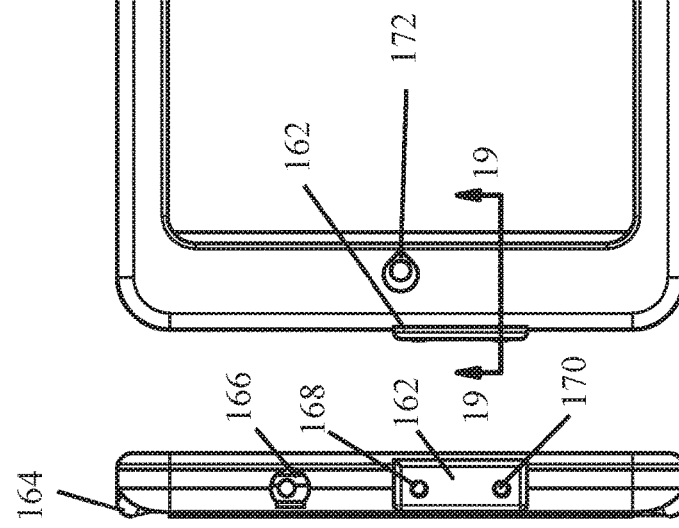
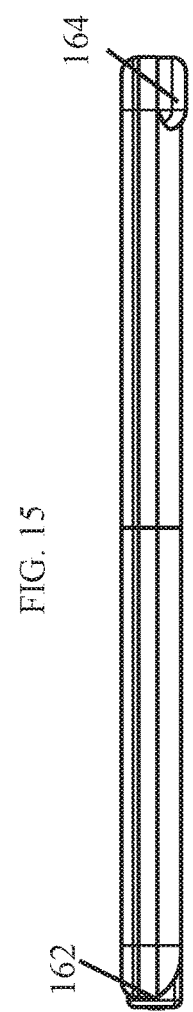
FIG. 13
FIG. 14
FIG. 15
FIG. 16
FIG. 17

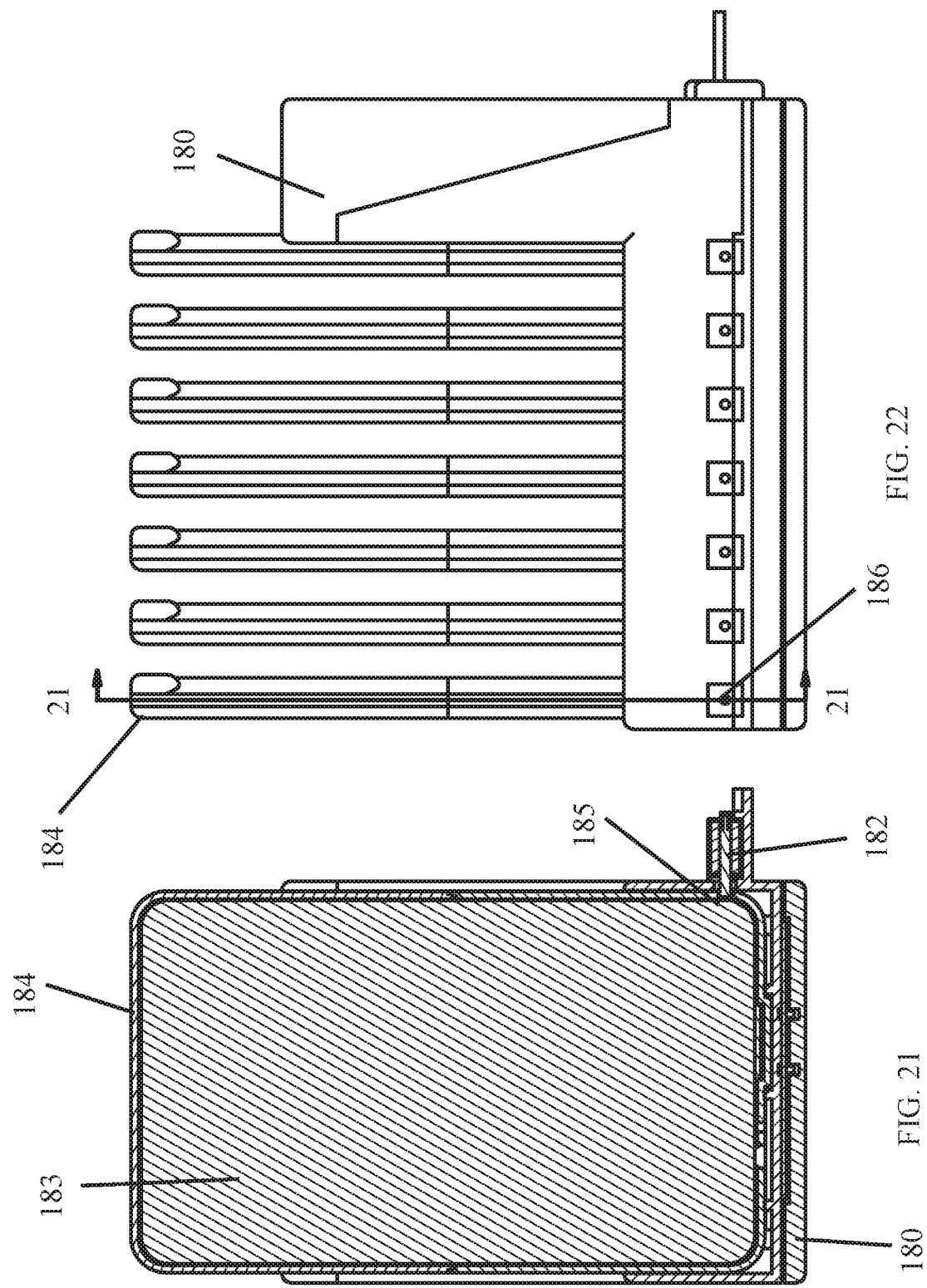

SECURE CHARGING SYSTEM FOR ELECTRONIC DEVICES

CROSS-REFERENCE TO RELATED APPLICATIONS

This application claims priority to and is a continuation in part of U.S. patent application Ser. No. 16/033,045 entitled "SECURED STORAGE FOR ELECTRONIC DEVICES" that was filed on Jul. 11, 2019 that issued as U.S. Pat. No. 10,678,302 on Jun. 9, 2020, that is a continuation in part of U.S. patent application Ser. No. 15/136,604 entitled "SECURED STORAGE FOR ELECTRONIC DEVICES" that was filed on Apr. 22, 2016 that issued as U.S. Pat. No. 10,225,734 on Mar. 5, 2019, which is a continuation in part of U.S. patent application Ser. No. 14/923,271 entitled "Protective Housing" that was filed on Oct. 26, 2015 that issued as U.S. Pat. No. 10,256,645 on Apr. 9, 2019 which is a continuation in part of U.S. patent application Ser. No. 14/869,592 entitled "Charging Unit and System" that was filed on Sep. 29, 2015 that issued as U.S. Pat. No. 9,917,455 on Mar. 13, 2018.

STATEMENT REGARDING FEDERALLY SPONSORED RESEARCH OR DEVELOPMENT

Not Applicable.

REFERENCE TO A MICROFICHE APPENDIX

Not Applicable.

RESERVATION OF RIGHTS

A portion of the disclosure of this patent document contains material which is subject to intellectual property rights such as but not limited to copyright, trademark, and/or trade dress protection. The owner has no objection to the facsimile reproduction by anyone of the patent document or the patent disclosure as it appears in the Patent and Trademark Office patent files or records but otherwise reserves all rights whatsoever.

BACKGROUND OF THE INVENTION

I. Field of the Invention

In large organizations such as businesses, schools, hospitals, nursing homes, and jails, it is becoming increasingly common to have a significant number of mobile electronic devices which need to be charged on a regular basis. Current art for charging systems provides for basic charging but not comprehensive administration and control of mobile electronic charging throughout the organization. The present invention provides for large scale control of mobile device charging not possible with current art.

The present invention relates to a security system for charging and tracking tablets, smart phones, mobile computing devices, mobile electronic devices, and other electronic devices to allow remote control and management of the charging activity and mobile electronic device. The secure charging system may also be implemented with an identity system for the electronic device. In another embodiment, the secure charging system may securely store the electronic device to prevent unauthorized access to the device.

The secure charging system provides a method of charging the electronic device and a method of communication for remote administration. In one embodiment, the secure charging system may be implemented with communication capabilities to a central server and respond to commands from the central server. In another embodiment, the secure charging station may be implemented with peer-to-peer communications between charging stations.

In some embodiments, the secure charging system provides a lock that locks the device into position. The lock controls access to the device. If the user is granted access, the lock of one embodiment retracts within housing to allow removal of the device from the housing. To secure the device, the lock extends from the housing towards the device.

In some embodiments, the secure charging system may accept commands and utilize a central server to coordinate charging activities across multiple chargers which are physically separated from one another. In one embodiment, the secure charging system could disable charging for one or more electronic devices based on a remote command. In another embodiment, the secure charging system could report all electronic devices currently being charged.

In one embodiment, the secure charging system may be implemented with an identification system to identify electronic devices attempting to charge. In this embodiment, charging could be enabled or disabled based on the identity of the electronic device and the rules established by administrative personnel. In some embodiments, the secure charging system reports electronic device identity and charging status to a central server. In some embodiments, the charging system may bill or track electricity usage based upon information collected and/or reported by the secure charging system. In other embodiments, the secure charging system may send alerts if an electronic device has not been returned to a charger within a specified amount of time.

The server of one embodiment tracks usage of the devices. The server tracks the devices that are checked out and the devices that have been returned. The server generates reports identifying the status of the devices. Such statuses include but are not limited to devices within the base, devices out of the base, devices in the base not charging, devices charging in the base, and updates to the device. The server generates reports identifying the status of the devices and the date and the time of the status of the device.

In some embodiments, the secure charger may be equipped with cameras to identify persons retrieving mobile electronic devices from the secure charger. In some embodiments, cameras may take pictures of returned mobile electronic devices for damage assessment and transmit the pictures to a central server for evaluation.

In some embodiments, a touchscreen for entry is attached to the secure charger for entry of user authentication information. In other embodiments, the charger integrates a biometric device such as a camera, microphone, fingerprint reader, or the like, for authentication.

The present invention also cleans, sanitizes, and/or disinfects the mobile computing device, such as the tablets, when the mobile computing device is placed within the secure charger. The housing applies a sanitizing spray, such as a disinfectant to the device(s). In another embodiment, a sanitizing light, such as a UV light, shines on the devices to disinfect the device.

II. Description of the Known Art

Certain problems exist with the known art. Known charging systems provide unfettered and unmonitored access to charging services after an electronic device is physically connected to the charger. Known charging systems do not allow remote management of chargers by administrative personnel. Known charging systems do not allow multiple chargers which are physically separated to act in unison as a single charging system.

Known charging systems for electronic devices do not allow security rules to be enacted to prevent unauthorized charging of devices. Known charging systems do not allow a central server to maintain charging rules which can automatically enable or disable charging to specific electronic devices or specific physical charging connections. Known charging systems cannot aggregate data into an analytical engine to determine costs or usage across multiple distributed chargers.

Known charging systems for electronic devices do not monitor when devices are charging or stop charging. Known charging systems do not report to a central server for tracking usage or billing activities. Known charging systems for electronic devices do not monitor the physical condition of the electronic device or assess it for damage while using the charging system.

Known charging systems for electronic devices do not disable the electronic device if the electronic device is not returned to a specified charger within a defined period of time. Known charging systems do not send alerts to administrative personnel when an electronic device has not been returned to a charger within a defined period of time.

Known charging systems for electronic devices do not take pictures of mobile electronic devices inserted for charging.

The present invention is needed to provide a unique charging system that efficiently manages large numbers of electronic devices within an organization such as a business, a school, or jail. The present invention is needed to prevent unauthorized charging and provide auditable rules-based security for charging electronic devices. The present invention is needed to enforce electronic device usage limits based on physical return of electronic devices to a charging station according to established rules.

SUMMARY OF THE INVENTION

The present invention relates to secured charging for charging tablets, smart phones, mobile electronic devices, mobile computing devices, and other electronic devices. The mobile computing devices may include, but are not limited to, tablets, smart phones, iPads, iPods, iPhones, Android devices, televisions, DVD playback devices, Raspberry Pi, Arduino device, radios, MP3 players, wearable devices, fitness trackers, digital audio players, and digital media players. The secured charging system of the present invention limits access to charging until centrally controlled administrative rules are met. The rules may be applied by a rules logic system implemented locally or remotely, such as on a server. The rules logic system confirms that the authenticated user and the identified device meet the rules of the facility. If the rules are met, the rules logic system provides an unlock message instructing the base to unlock the identified device to the authenticated user.

The secure charging system of one embodiment provides electrical charging capabilities when the electronic device is placed onto the secure charger. The present invention may provide charging contacts of the charger that contact that touch the electrical charging contacts of a mobile electronic device when the device is properly placed onto the secure charger. Other embodiments may implement wireless charging as discussed below such as inductive charging.

In one embodiment, the secure charger identifies the mobile electronic device by exchanging identification data with the device electronically and communicates with a central server. The central server compares the secure charger request against a database of charging rules which apply to the specific mobile electronic device. If the rules are met, the central server communicates to the secure charger that charging is allowed for the device. Once the secure charger receives authorization from the central server, electricity flows through the charging conductors between the secure charger and the mobile electronic device for charging the battery of the mobile electronic device.

In another embodiment, the secure charger may also be implemented with a locking system for securing the mobile electronic device until authentication of the user and device are completed by an authentication system. Such an authentication system may be implemented locally or remotely, such as on a server. The authentication system verifies the identity of the user.

A rules logic system, such as a server, may apply the rules of the system. Such rules may be implemented by the facility. Once verified against a database of rules, the base unlocks the mobile electronic device for removal of the device from the secure charger.

In one embodiment, an administrator inputs charging rules into a central server database using a web form. The administrator specifies a rule defining the devices allowed to charge, the times charging is allowed, and the users allowed to unlock the mobile electronic device from the secure charger. Upon request by the secure charger, the central server uses the predefined rules setup by the administrator to determine whether the mobile electronic device should be charged while connected to the secure charger. In this embodiment, the central server also authenticates end users requesting the release of a mobile electronic device locked in the secure charger and determines whether to unlock the mobile electronic device based on the rules established by the administrator.

Controlling the charging of the devices enables administrators to control usage of the devices that may not be connected to a network. Administrators may selectively charge devices to control usage of the devices. Without a charge, users cannot use or misuse the devices. Administrators simply stop charging selected devices to limit use of the device.

Passwords have traditionally controlled access to a WIFI system. However, the users can access, use, and misuse the device without WIFI access. The present invention limits usage of electricity to eventually limit the usage of unauthorized devices. If the unauthorized devices cannot be charged, usage of the unauthorized devices will eventually cease.

Most devices provide a port for accepting a charger. The charging port may accept USB, USB micro, USB mini, Lightning, or other electrical insertion connection. New connections with new ports will more than likely be developed in the future. In some embodiments, a charging adapter of the present invention inserts into the port of the device. The charging adapter can be modified to function with the new ports and electrical insertion connections. In other embodiments, charging could be provided by inductive charging pads, ultrasonic transmission, light transmittal, or other energy transmittal mechanisms that charge mobile electronic devices.

In some embodiments, the charging system also provides a protective housing for the device. The housing is keyed to the charging station to orient the device when inserting the device into the charging station. The charging adapter is secured within the housing to enable charging of the device. Keyed locks or audible alarms could increase the security features of the present invention.

The housing of one embodiment protects the device from damage. The housing may also prevent access to certain features of the device. Eliminating access to these features prevents users from gaining unauthorized access to the device. The housing also prevents users from resetting the device to allow unfettered access to the user.

It is an object of the present invention to provide centrally controlled mobile electronic device locking.

It is an object of the present invention to track and record activity related to mobile electronic device insertion into and removal from a plurality charging bases.

It is an object of the present invention to provide centrally controlled mobile electronic device charging.

It is an object of the present invention to enable charging to mobile electronic devices only when administrative rules have been met.

It is an object of the present invention to track and record activity related to mobile electronic device charging and present it in usable form for billing or other administrative purposes.

It is an object of the present invention to prevent charging of mobile electronic devices to unapproved devices connected to a secure charger.

It is an object of the present invention to securely charge an approved mobile electronic device within secure storage.

It is an object of the present invention to provide a housing that accepts a lock to secure the electronic device.

It is an object of the present invention to secure an electronic device not stored in a specialized case within the secure storage.

It is an object of the present invention to limit access to the electronic device by storing the device within the secure storage.

It is an object of the present invention to monitor usage of the electronic device by maintaining records of users who remove the device from the secure storage.

It is an object of the present invention to monitor charging of the electronic device by maintaining records of device presence on the secure charger and activation of charging to the device.

It is an object of the present invention to control access to the electronic device by restricting user's access to the device from the storage.

It is an object of the present invention to control access to the electronic device by allowing user's access to the device from the storage.

It is another object of the present invention to simplify the process of administrating the charging of multiple mobile electronic devices across an organization.

It is another object of the present invention to reduce the costs associated with charging multiple devices.

It is another object of the present invention to reduce unauthorized use and misuse of devices by restricting charging a mobile electronic device which has not been approved by the organization.

It is another object of the present invention to charge multiple mobile electronic devices within a single charging station.

It is another object of the present invention to limit access to selected users of the mobile electronic device.

It is another object of the present invention to limit access to selected features of the mobile electronic device.

It is another object of the present invention to clean, disinfect, and/or sanitize the mobile electronic device.

These and other objects and advantages of the present invention, along with features of novelty appurtenant thereto, will appear or become apparent by reviewing the following detailed description of the invention.

BRIEF DESCRIPTION OF THE DRAWINGS

In the following drawings, which form a part of the specification and which are to be construed in conjunction therewith, and in which like reference numerals have been employed throughout wherever possible to indicate like parts in the various views:

FIG. 5 is a rear view thereof;

FIG. 6 is a left side view thereof, the right side view being a mirror image of the left side view;

FIG. 7 is a front view thereof;

FIG. 8 is a bottom view thereof;

FIG. 13 is a left side view thereof;

FIG. 14 is a bottom view thereof;

FIG. 15 is a front view thereof;

FIG. 16 is a top view thereof;

FIG. 17 is a right side view thereof;

FIG. 21 is a partial view of one embodiment of the present invention;

FIG. 22 is a right side view thereof;

DETAILED DESCRIPTION

Figure 1:
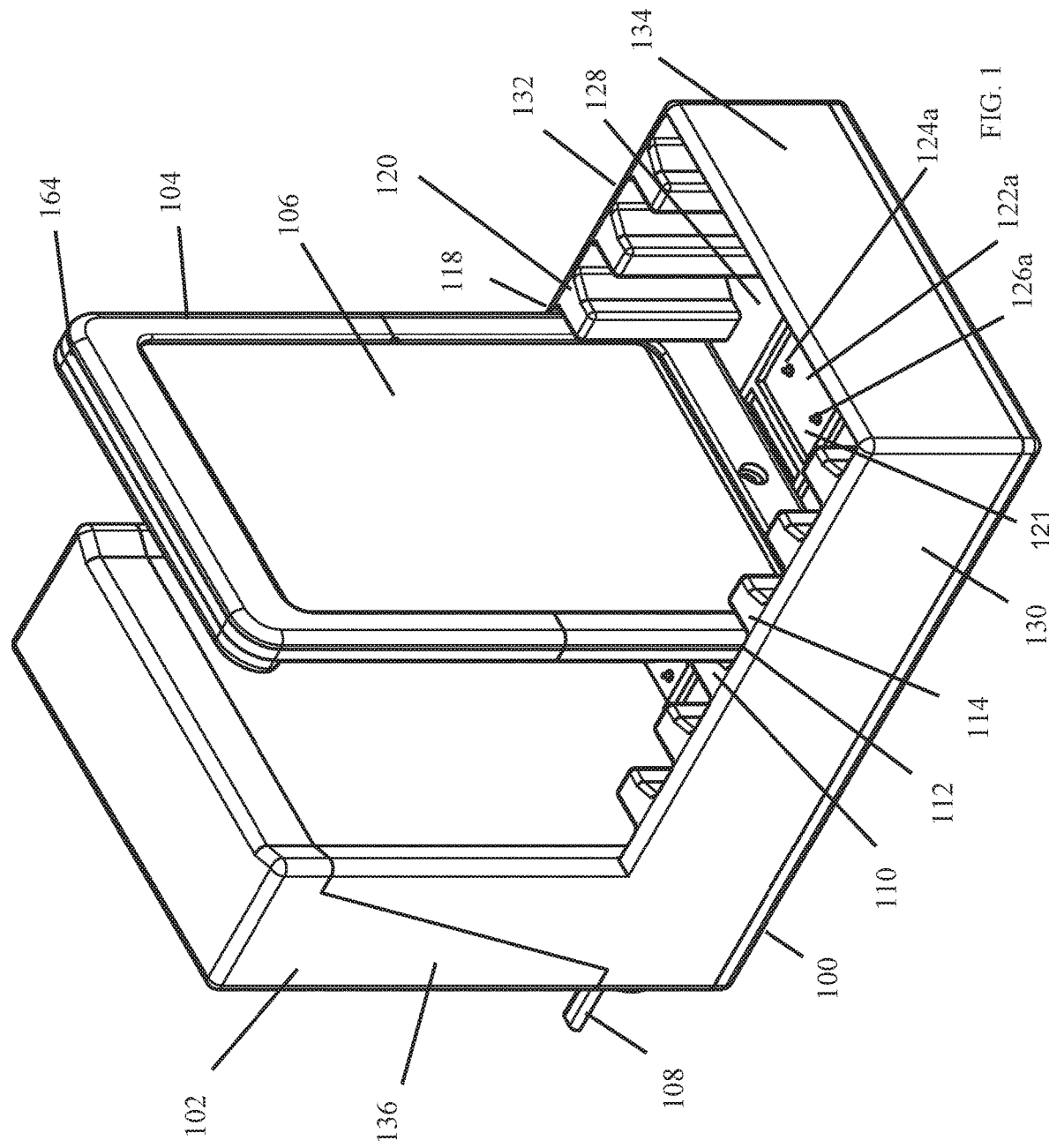
FIG. 1 is an environmental view of one embodiment of the present invention.
Figure 2:
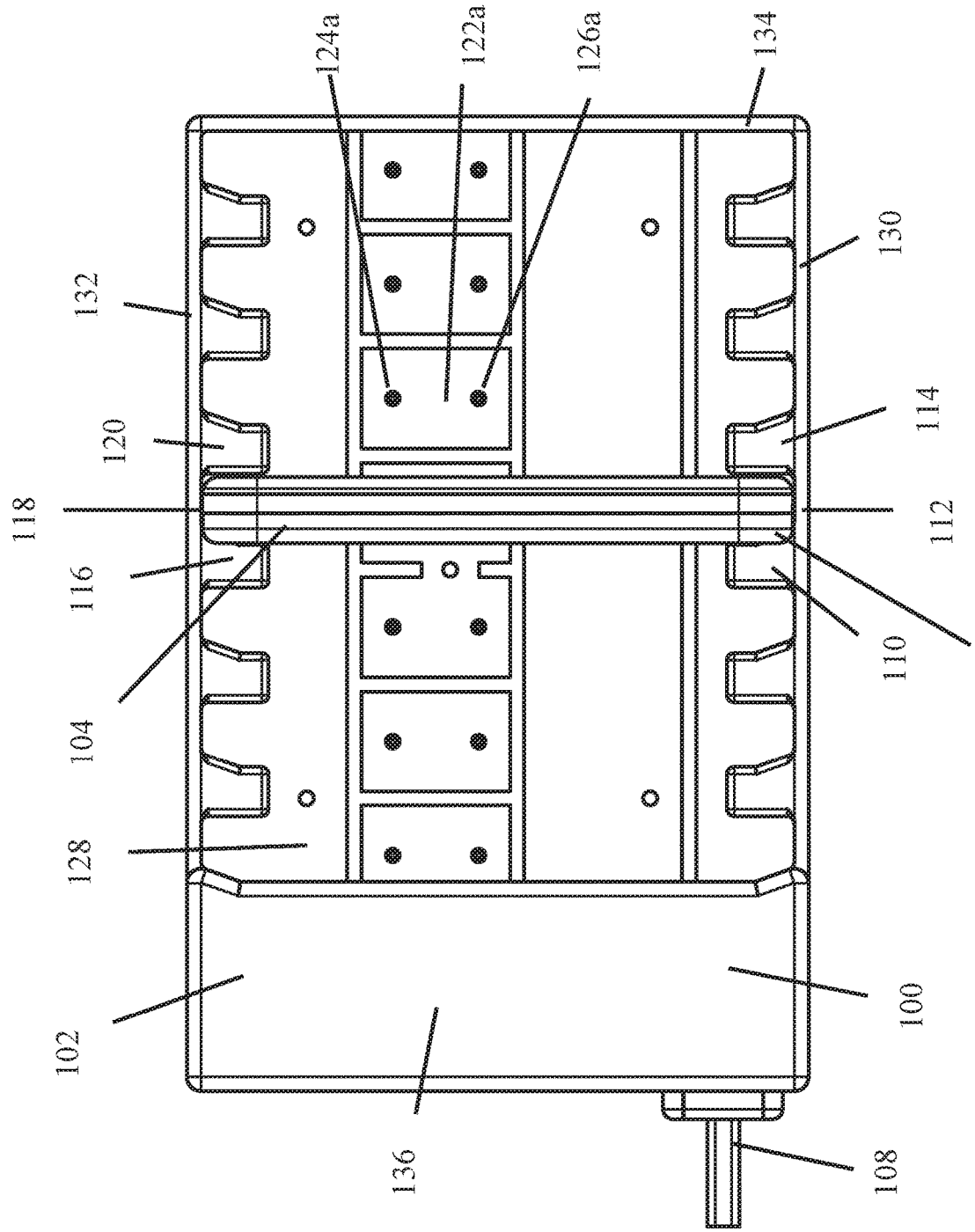
FIG. 2 is an environmental view thereof.

FIGS. 1 and 2 show an environmental view of one embodiment of the charging system 100 for storage of a mobile computing device. The charging system 100 provides a charging base 102 and a housing 104 that at least partially encloses a mobile computing device 106. The present invention has been described as operating for a mobile computing device. The mobile computing devices may include, but are not limited to, tablets, smart phones, iPads, iPods, iPhones, Android devices, televisions, DVD playback devices, Raspberry Pi, Arduino device, radios, MP3 players, wearable devices, fitness trackers, digital audio players, and digital media players. The charging system 100 simplifies the process of charging the devices by removing the need to insert a plug into the port of the device to charge.

Most devices 106 provide a port for accepting a charger. The port may accept USB, USB micro, USB mini, Lightning, or any other electrical insertion connection. A charging adapter of the present invention inserts into the port of the device. The housing secures the charging adapter within the port. The charging adapter provides two charging contacts that provide power to the battery of the device.

The charging system 100 provides a housing 104 for the electronic device 106 and a charging base 102 designed to receive the housing 104. The charging base 102 is configured to accept the housing 104 in a set orientation, preferably a charging orientation. The charging base 102 provides charging contacts that connect to a power source via power cord 108. The charging base 102 accepts housing 104 in a charging orientation that will allow for charging of the device 106.

The charging base 102 aligns charging contacts of the charging adapter with charging contacts of the charging base 102. Insertion of the housing 104 into the charging base 102 in the charging orientation completes the circuit of the charging contacts to charge the device 106.

In one embodiment, retention arms 110, 114, 120 protrude laterally from an interior portion of a first wall 130 and a second wall 132 located opposite the first wall 130. The retentions arms 110, 114, 116, 120 support the housing 104 when inserted into the charging base 102.

In one embodiment, the retention arms 110, 114, 116, 120 provide a unique shape to allow insertion of the housing 104 into the charging base 102 in a charging orientation as shown in FIGS. 1 and 2. The retention arms 110, 114, 116, 120 of such an embodiment prevent insertion of the housing 104 into the charging base 102 in orientations that will not charge device 106. Such a configuration promotes charging of device 106 when inserted into the charging station 102.

The charging base 102 provides at least two charging contacts 124, 126 for contacting the charging contacts of the charging adapter. Electricity flows from the charging base 102 to the device 106 via the charging contacts 124, 126 located within charging aperture 122. The charging aperture 122 of one embodiment is keyed to accept the insertion of at least a portion of the housing 104 where the charging adapter is located.

In one embodiment, the retention arms 110, 114, 116, 120 support the housing 104 and device 106 when the device 106 is inserted into the charging station 102. The retention arms 110, 114, 116, 120 align the charging contacts of the charging adapter with the charging contacts 124, 126 of the charging base 102. The device 106 can then charge properly without insertion of a cord into the port. The contact between the charging contacts supply sufficient power to charge the device 106 when the charging base 102 is plugged into a power source.

The power cord 108 attached to a power source supplies power to the charging contacts 124, 126 within the base. The charging station 102 is keyed to accept insertion of the device 106 in a set orientation, such as the charging orientation. The keying of the charging station 102 prevents users from incorrectly inserting the device 106 into the charging station 102. The retention arms 110, 114, 116, 120 create retention apertures 112, 118 that accept the housing 104 in the charging orientation.

The retention arms 110, 114, 116, 120 and retention apertures 112, 118 accept the housing 104 in a charging orientation. The housing 104 positioned in the charging orientation aligns the charging contacts. The retention arms 110, 114, 116, 120 prevent insertion of the housing 104 into the charging station 102 in an orientation in which the charging contacts cannot complete the circuit to transfer electricity to the device.

The charging system 100 also provides a protective housing 104 for the device 106. The housing 104 is keyed to the charging station 102 to orient the device 106 when inserting the device 106 into the charging station 102. A blocking head 164 of the housing 104 is sized not to be inserted into the receiving apertures 112, 118. In one embodiment, the blocking head 164 may be sized larger than the receiving apertures 112, 118. In another embodiment, the blocking head 164 protrudes from the housing 102 to prevent insertion.

As discussed above, the port of the device 106 is usually located at the bottom of the device 106. The charging adapter and charging contacts of such a device would also be located at the bottom of housing 104 and device 106. To complete the circuit, the charging contacts 124, 126 protrude upward from the floor 128 of the charging base 102. The blocking head 164 of such an embodiment would be located at the top of the housing 104 to prevent insertion of the top of the housing 104 into the charging stations 102.

The charging station 102 provides four walls, walls 130, 132, 134, 136. The walls 130, 132, 134, 135 provide sufficient space between the walls for insertion of the housing 104 into the charging station 102 in the charging orientation.

Figure 3:
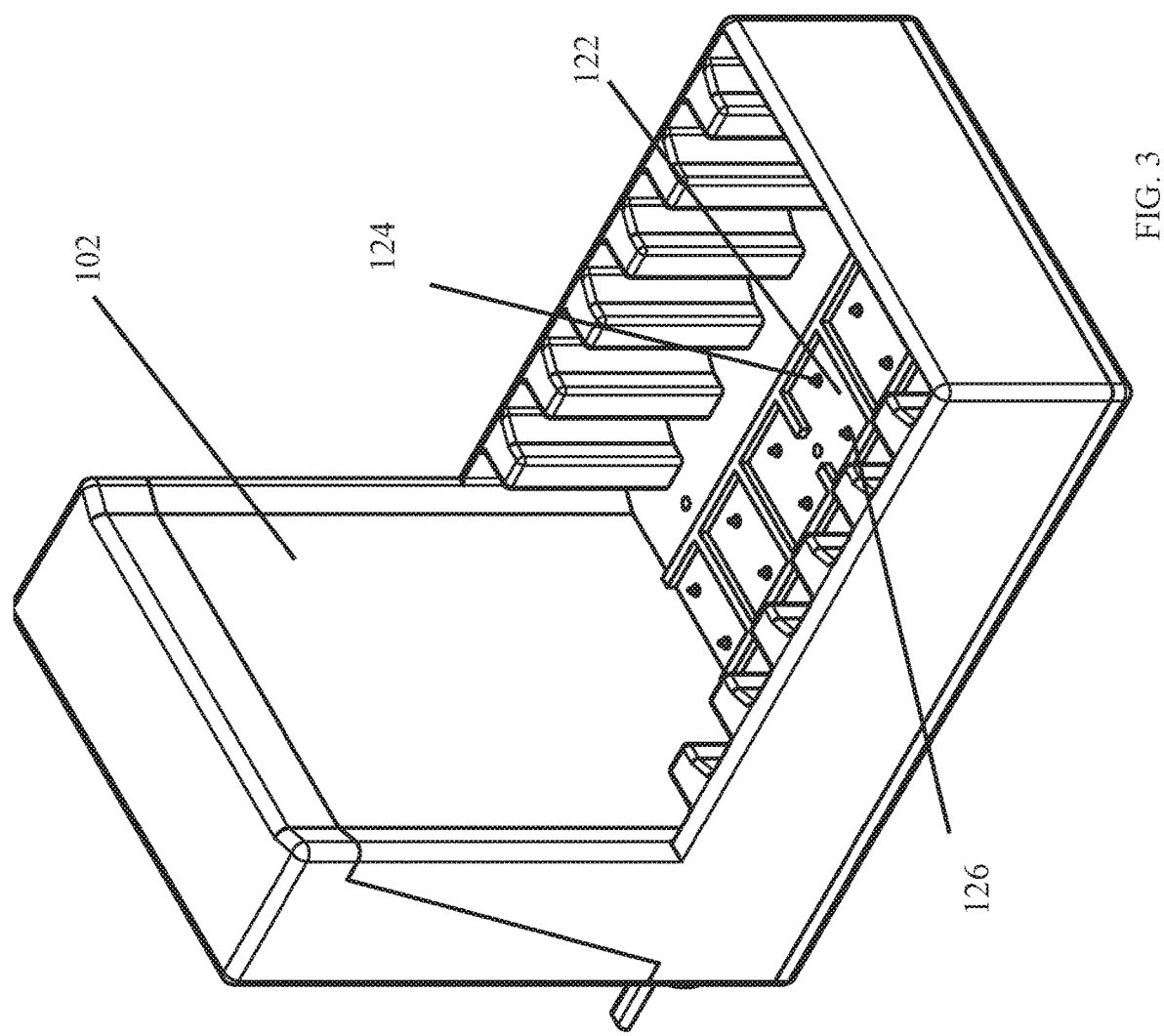
FIG. 3 is a perspective view of the charging station of one embodiment of the present invention.
Figure 4:
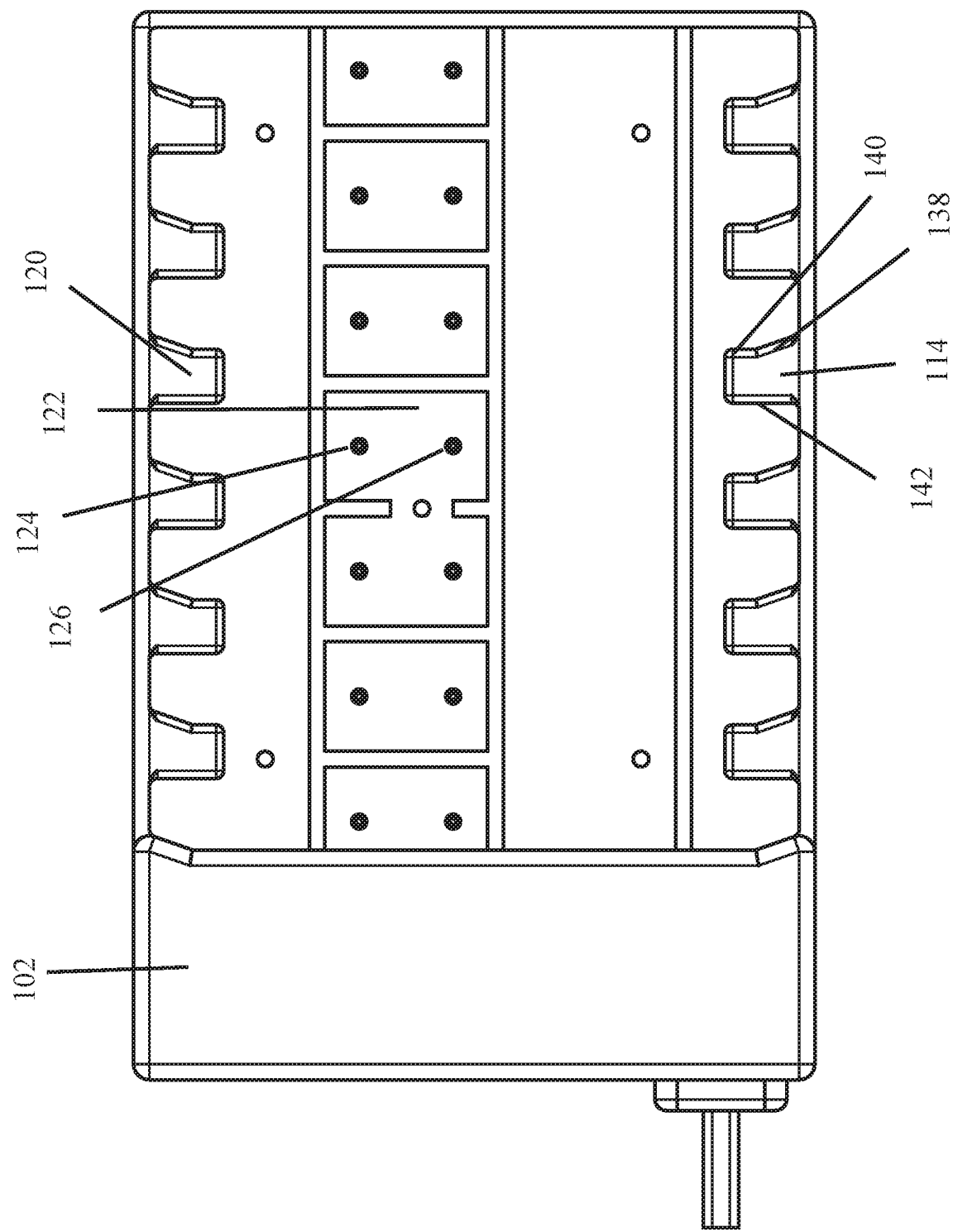
FIG. 4 is a top view thereof.

FIGS. 2-4 show the keying of the housing 104 with receiving apertures 118, 120. A bottom portion of the housing 102 is inserted into the receiving apertures 112, 118 between retention apertures 110, 114, 116, 120. Charging contacts 124, 124a, 126, 126a at charging aperture 122, 122a are exposed through the floor 128 of the charging base 102.

Blocking head 164 is sized not to pass into receiving apertures 118, 120. As shown in FIG. 2, blocking head 164 is larger than receiving apertures 118, 120. Retention arms 110, 114, 116, 120 provide a retention elbow 138, a retention finger 140, and retention back 142. Retention elbow 138 angles into the receiving aperture 118, 120 to reduce the size of the receiving apertures 118, 120. The receiving apertures 118, 120 narrow at the retention elbow 138. The reduced size of the receiving apertures 118, 120 prevents insertion of the blocking head 164 into the receiving apertures 118, 120.

FIGS. 5-8 show different views of the charging base 102. Walls 120, 132, 134, 136 define the area in which the housings may be stored. In one embodiment, power cord 108 secures to the power source for charging the devices.

Figure 9:
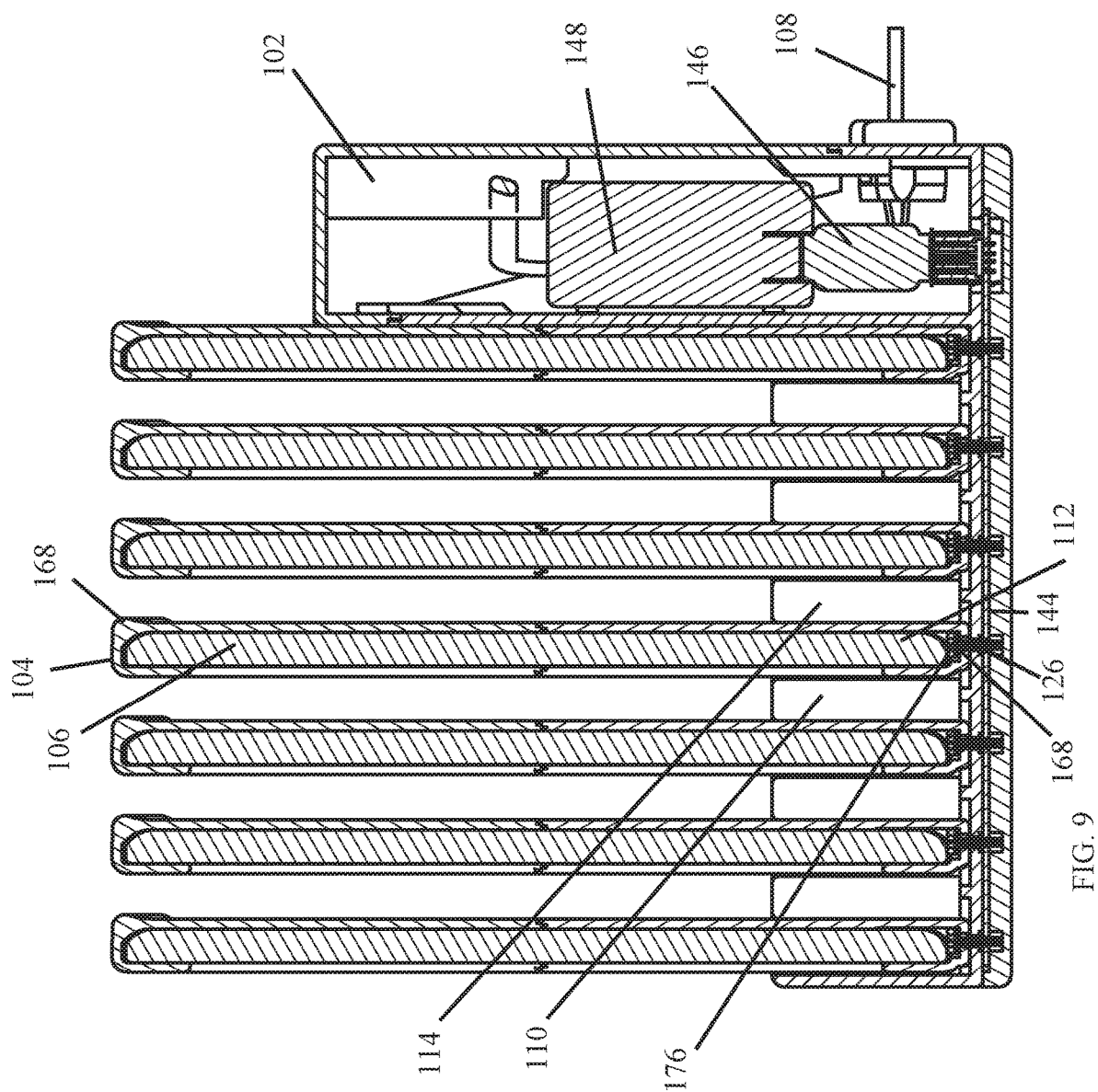
FIG. 9 is a sectional view of one embodiment of the present invention.
Figure 10:
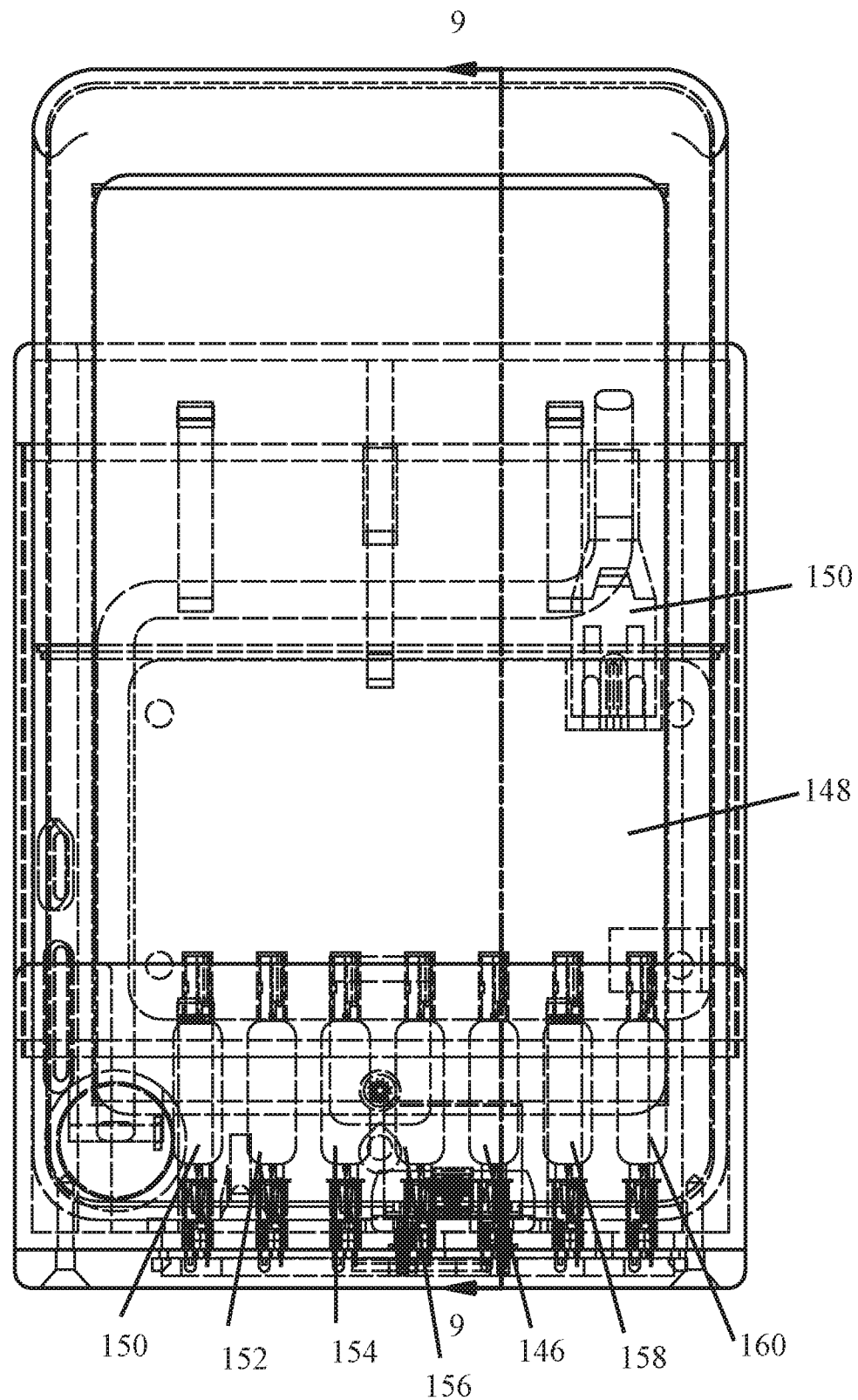
FIG. 10 is a sectional view thereof.

The charging station 102 houses the conductors and adapters needed to charge the devices as shown in FIGS. 9 and 10. The charging station 102 accepts multiple devices 106 and housings 104 for charging multiple devices 106 at a time. FIG. 9 emphasizes the fact that blocking head 168 protrudes outward to prevent insertion of the blocking head 164 into receiving aperture 112.

The retention fingers 110, 114 direct the charging adapter 174 within housing 104 towards charging contacts 126. Charging contacts 168 of charging adapter 174 complete the circuit with charging contacts 126 of the charging base 102. Completing the circuit charges the devices 106 when the charging base 102 is connected to a power source.

Conductor 144 connects the charging contacts 126 with adapter 146, such as a male to male USB adapter. Adapter 146 is inserted into charger 148 which is a multiport USB charger. Power cord 108 supplies power to charger 148 which transfers power to adapter 146. The electricity then flows through conductor 144 and charging contacts 126 to charging adapter 176.

Figure 11:
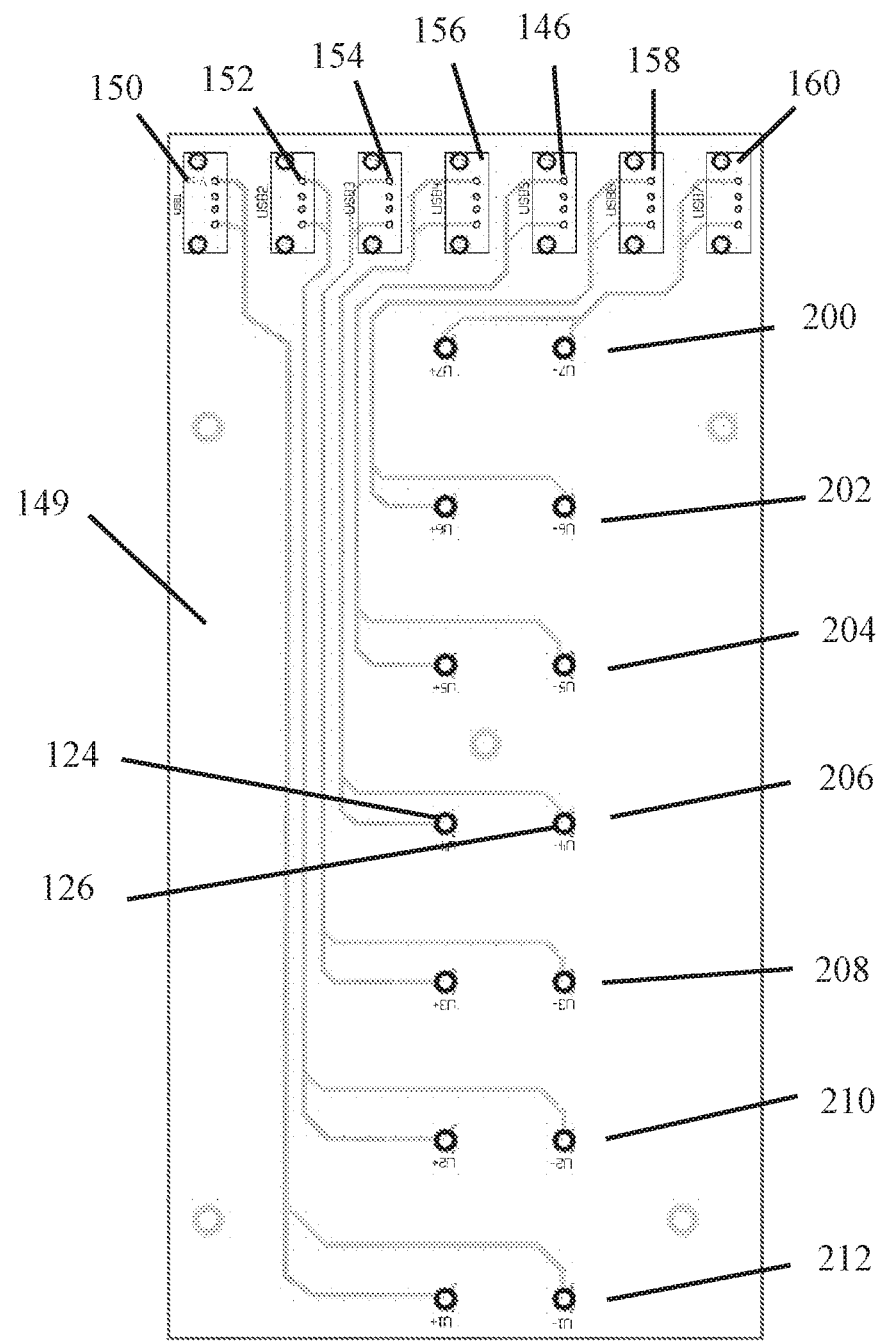
FIG. 11 is a schematic view of one embodiment of the present invention.
Figure 12:
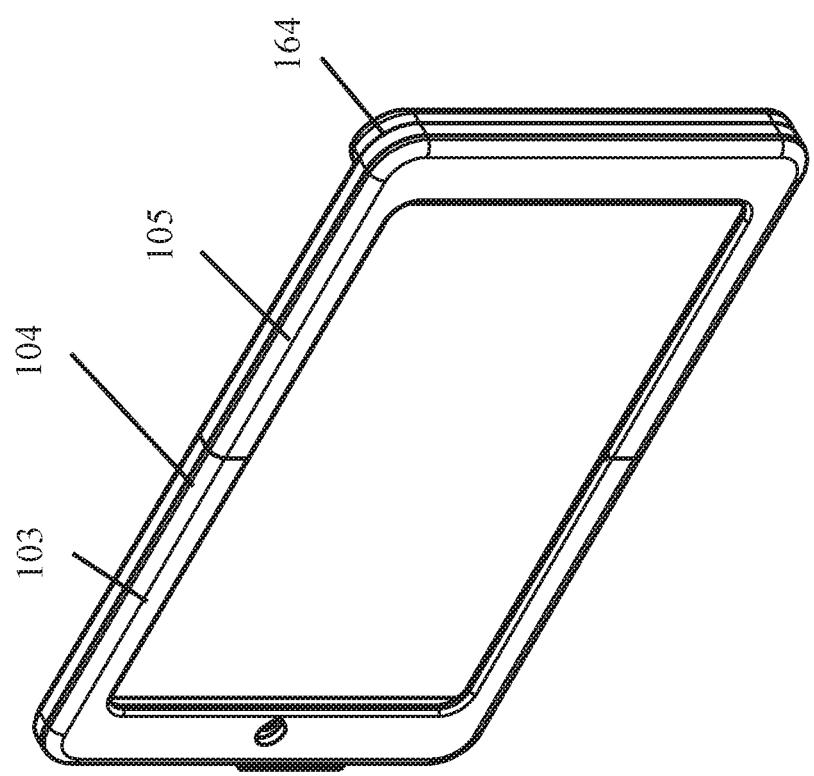
FIG. 12 is a perspective view of a housing of one embodiment of the present invention.
Figure 18:
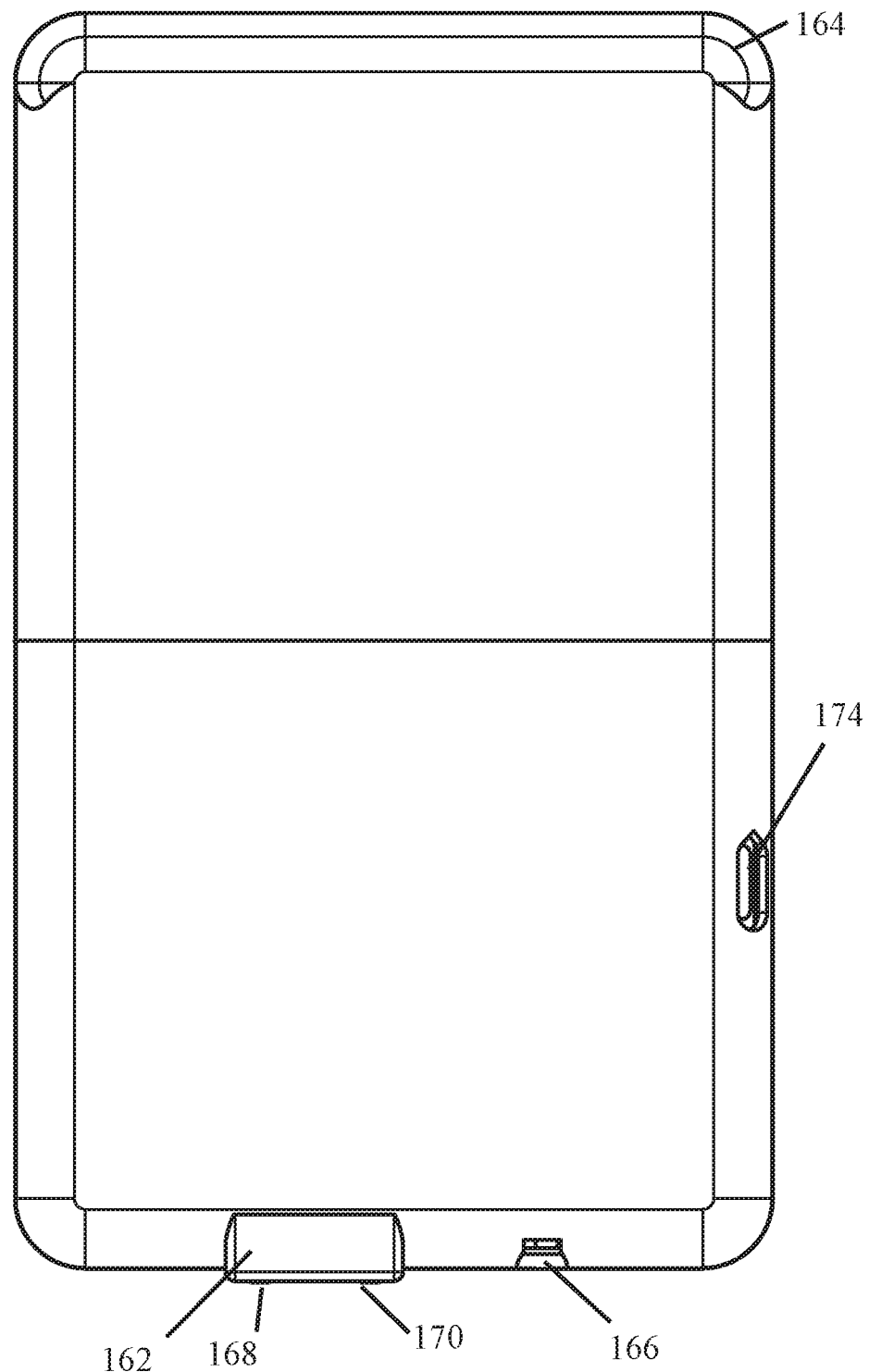
FIG. 18 is a rear view thereof.

FIGS. 10-11 show the connection of adapters 146, 150, 152, 154, 156, 158, 160 into the charger 148. Power cord 150 plugs into charger 148. Each adapter 146, 150, 152, 154, 156, 158, 160 attaches to conductors that supply power to charging contacts 124, 126.

As shown in FIG. 11, conductors connect each adapter 146, 150, 152, 154, 156, 158, 160 to sets of charging contacts 200, 202, 204, 206, 208, 210, 212. Each adapter 146, 150, 152, 154, 156, 158, 160 attaches to two conductors which attach to each charging contact of the set of charging contacts. Each set of charging contacts 200, 202, 204, 206, 208, 210, 212 provides a charging contact similar to charging contacts 124, 126. The set of charging contacts 200, 202, 204, 206, 208, 210, 212 complete an electric circuit with the charging adapter to charge the device.

FIGS. 12-18 show the housing 104 that at least partially encloses the device. The housing of one embodiment provides a lower body 103 and an upper body 105. The housing of other embodiments may be constructed from a variation of other designed pieces to at least partially encase the device. The housing 104 protects the device 106 from damage. The housing 104 also prevents access to certain features of the device 106. Eliminating access to these features prevents users from gaining unauthorized access to the device 106. The housing 104 also prevents users from resetting the device 106 to allow unfettered access to the user.

In one embodiment, the housing is constructed from a rigid material. A shock absorbing material may be added to the housing to provide additional support. In one embodiment, the housing is constructed from a hard plastic. The housing could also be constructed from aluminum or other metal. The housing is constructed from a material that will adequately protect the device. The housing of one embodiment is also constructed from material sufficient to prevent access to some features of the device.

The housing 104 of one embodiment is designed to be tamper proof. While certain housings and cases are designed to be removed and reinstalled, the housing 104 of one embodiment is designed to be difficult to remove. The lower body 103 and upper body 105 are secured to each other with an adhesive or welded together to deter removal of the housing 104. Other embodiments may secure the housing together via security screws, keyed locks, and/or other tamper proofing methods.

If a user removes the housing 104, the users will recognize that the housing has been removed. The users can then reset the device to the appropriate settings and reattach the housing 104.

As discussed above, blocking head 164 protrudes outward from the housing. In such an embodiment, the top of the housing 104 has a larger surface area then the bottom of the housing. The housing provides apertures 166, 172, 174 that enable access to the device 106. In one embodiment, apertures 166, 172, 174 provide access to such features as the power button, audio output, and the camera. Aperture 166 provides access to the line out port for audio output. Aperture 172 provides access to the camera. Aperture 174 provides access to the power button.

The housing of one embodiment blocks buttons, inputs, and other access to the device. Some tablets and mobile computing devices allow a user to access features through such buttons and inputs. Limiting access to such buttons and inputs prevents users from reconfiguring the device or otherwise accessing restricted features of the device. The housing may block such buttons as the windows button and the volume controls. The housing may also block such inputs such as the charging/communication port and the storage slots that allow a user to increase the storage capacity of the device.

Foot 162 of housing 104 is keyed to fit within charging aperture 122. Foot 162 aligns charging contacts 168, 170 with charging contacts 124, 126. As discussed above, aligning charging contacts 124, 126, 168, 170 completes the circuit to allow charging of the device.

Figure 19:
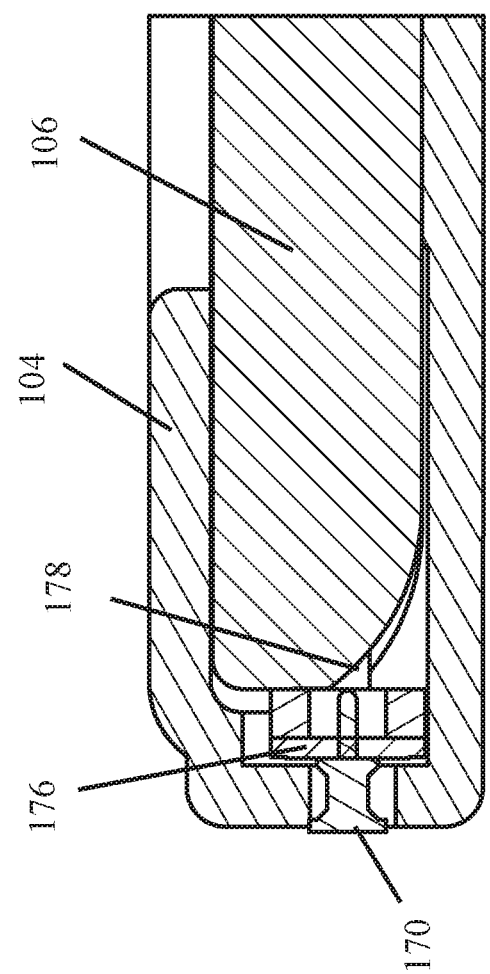
FIG. 19 is a sectional view thereof.
Figure 20:
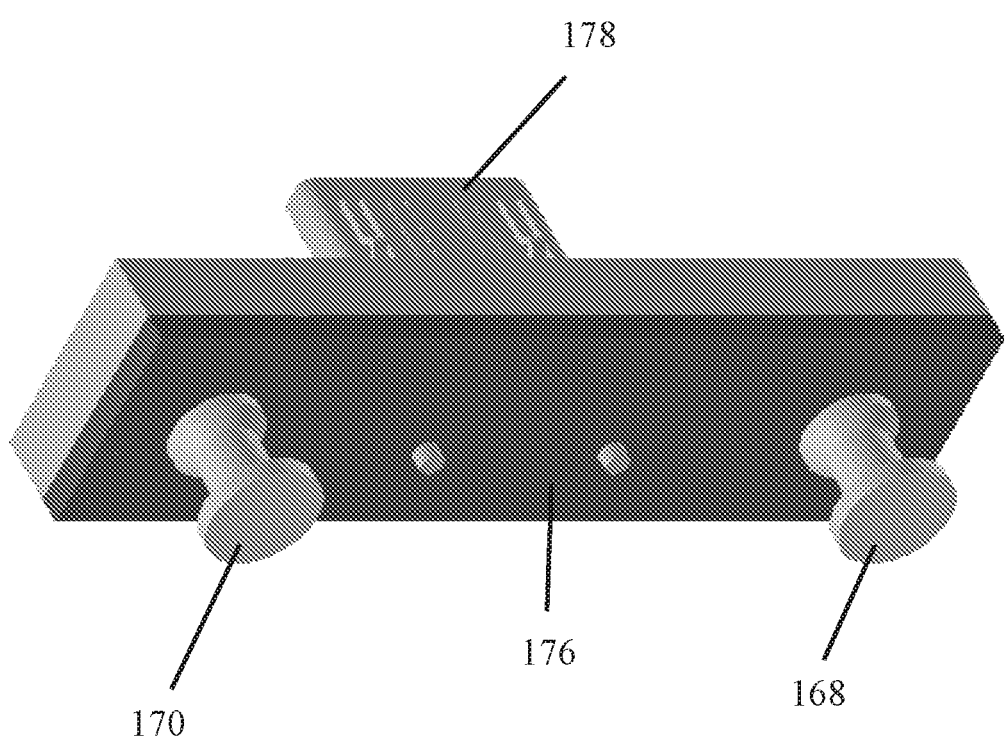
FIG. 20 is a perspective view of a charging adapter of one embodiment of the present invention.

FIGS. 19 and 20 show the charging adapter 176 and securing the charging adapter 176 within device 106. The charging adapter 176 is secured within the housing 104 to enable charging of the device. Male plug 178 inserts into the port of the device 106. Charging contacts 168, 170 of the charging adapter 174 extend into an aperture of the housing 104. The aperture of the housing enables the charging contacts 124, 126, 168, 170 to complete the circuit for charging the device 106.

In one embodiment, an identification system of the base communicates with the device to determine the device identifier of the device inserted into the base. A port of the device provides different pins capable of different functions such as charging the battery and transferring data as shown in FIGS. 35-38 and discussed below. At least one of these pins, a communication pin, provides a communication path between the device and the base. In one embodiment, the charging adapter serves as the communication system capable of identifying the device. The charging adapter of one embodiment provides contacts, such as a data contact, that communicates with the mobile device through the communication pin of the device. The data contact of the charging adapter contacts the communication pin of the mobile device. The communication system of one embodiment is implemented through the data contact.

The base of one embodiment communicates with the mobile device through data contact of the charging adapter and the communication pin of the device as shown in FIGS. 35-38. The base receives identification data from the device. The base determines the identification of the device. The server then instructs which devices to charge and which devices to release to specified users.

The charging contacts and orientations have been shown in one manner as shown in FIGS. 35-38. The placement of the charging contacts may vary according to the placement of the port and the size of the station. The charging station may be configured to accept the electronic device in other orientations that will allow for charging of the device.

The charging station may also serve as storage of the devices. The devices may be placed into the charging station and then locked within the charging station. Locking the devices in the charging station prevents unauthorized access and securely stores the devices within the charging station.

The charging station may also be implemented as a mobile charging station. Wheels may be attached to the charging station to assist with transporting the devices and the charging station. The wheels increase the mobility of the charging station. A handle may also be attached to the charging station for maneuvering the charging station.

In one embodiment, the electronic device may provide charging contacts without the charging adapter. The housing of such an embodiment provides an aperture that exposes the charging contacts for contact with the charging station. The housing may also be the casing that encases the internal components of the device.

FIGS. 21-26 show another embodiment of the charging station as secure storage base 180. Base 180 communicates with a server, such as a computer, to identify whether a device should be unlocked from the base 180. The base and server may communicate wirelessly or through a wired connection. Such communication may also occur across a network or across the Internet. A wireless communication device, including but not limited to NFC, WIFI, Bluetooth, and other wireless devices, may be provided with the base to allow wireless communication with the server.

Housing 184, shown in FIG. 21, at least partially encases an electronic device 183, such as tablets, smart phones, mobile computing devices, mobile electronic devices, and other electronic devices. The housing 184 inserts into secure base 180. A lock, such as a locking finger, locking magnet, locking device, or other locking mechanism, secures the electronic device within base 180. The lock may contact the electronic device or a housing at least partially encasing the electronic device. The lock may insert into an aperture of the device or the housing to secure the electronic device within the base.

In another embodiment, the lock contacts the device to prevent removal of the device from the base. The lock may be a locking finger that contacts the device. The locking finger adjusts between locked and unlocked. When locked, the locking finger is positioned above the charging end to contact the side of the device opposite of the charging side. When unlocked, the locking finger adjusts to allow removal of the device from the base. Such a version of the lock enables the lock to function without requiring a locking aperture.

In another embodiment, the base prevents removal of the device. The lock may pivot to prevent removal of the device from the base. The lock pivots between locked and unlocked. When locked, the lock is pivoted to secure the device within the base. When unlocked, the lock pivots to a position to enable removal of the device from the base. The removal of the device depends on the rotation of the lock.

In another embodiment, the lock may be implemented as a latch. The latch secures the device within the base. The latch adjusts between locked and unlocked.

The lock may also be a magnetic lock that adjusts between locked and unlocked. The lock secures the device within the base via the magnet. In one embodiment, the magnet secures the device within the base. The magnet may then be adjusted or deactivated for removal of the device from the base. In another embodiment, the magnet may attract and repel a locking finger for securing the device. The magnet may be an energized electromagnetic that secures the device. De-energizing the magnet enables removal of the device from the base.

The lock may also be a screw lock, twist lock, or hook lock. The screw lock twists into the mated locking aperture of the device or housing. In another embodiment, the screw lock may insert into a hole within the base. With the twist lock, a key inserts into a keyed hole and rotated for alignment with the keyed hole for removal of the device from the base. With the hook lock, a small hook rotates in a mating locking aperture on the device or housing.

Locking finger 182 inserts into a locking aperture 185 of housing 184 to secure the device 183 and housing 184 within base 180. The locking finger 185 adjusts between locked and unlocked. When locked, the locking finger 182 locks the device 183 within the base 180. The locking finger 182 when unlocked releases the device 183 from the base 180 to provide the user with access to the device 183.

In other embodiments, the locking finger 182 may insert directly into the locking aperture 185 of the device 183 to secure the device within the base. In another embodiment, the locking finger 182 may simply contact the device to secure the device within the base.

FIG. 22 shows an embodiment of base 180 capable of storing multiple electronic devices within base 180. The base 180 may store one device or multiple devices. In one embodiment, the base 180 receives housing 184 similar to the housing 104 described above for the charging station.

FIG. 22 also shows the access status or charging status with a status light 186. The status light 186 indicates whether the device is available for access. In one embodiment, each light 186 represents access to a device. The status light 186 may be on or off depending on whether the user can access the device 183 associated with the light 186. In another embodiment, the color of the light 186 may indicate whether the user may access the device 183.

In another embodiment, the status light 186 indicates whether the device 183 is charged or charging. As discussed above, the status light may be on indicating that the device is charging. In another embodiment, the status light may be on indicating that the device is fully charged. Another embodiment may change the color of the status light to indicate whether the device 183 is charging or fully charged. The status light may also identify the the device assigned by the system for the user to access and remove from the base.

Figure 23:
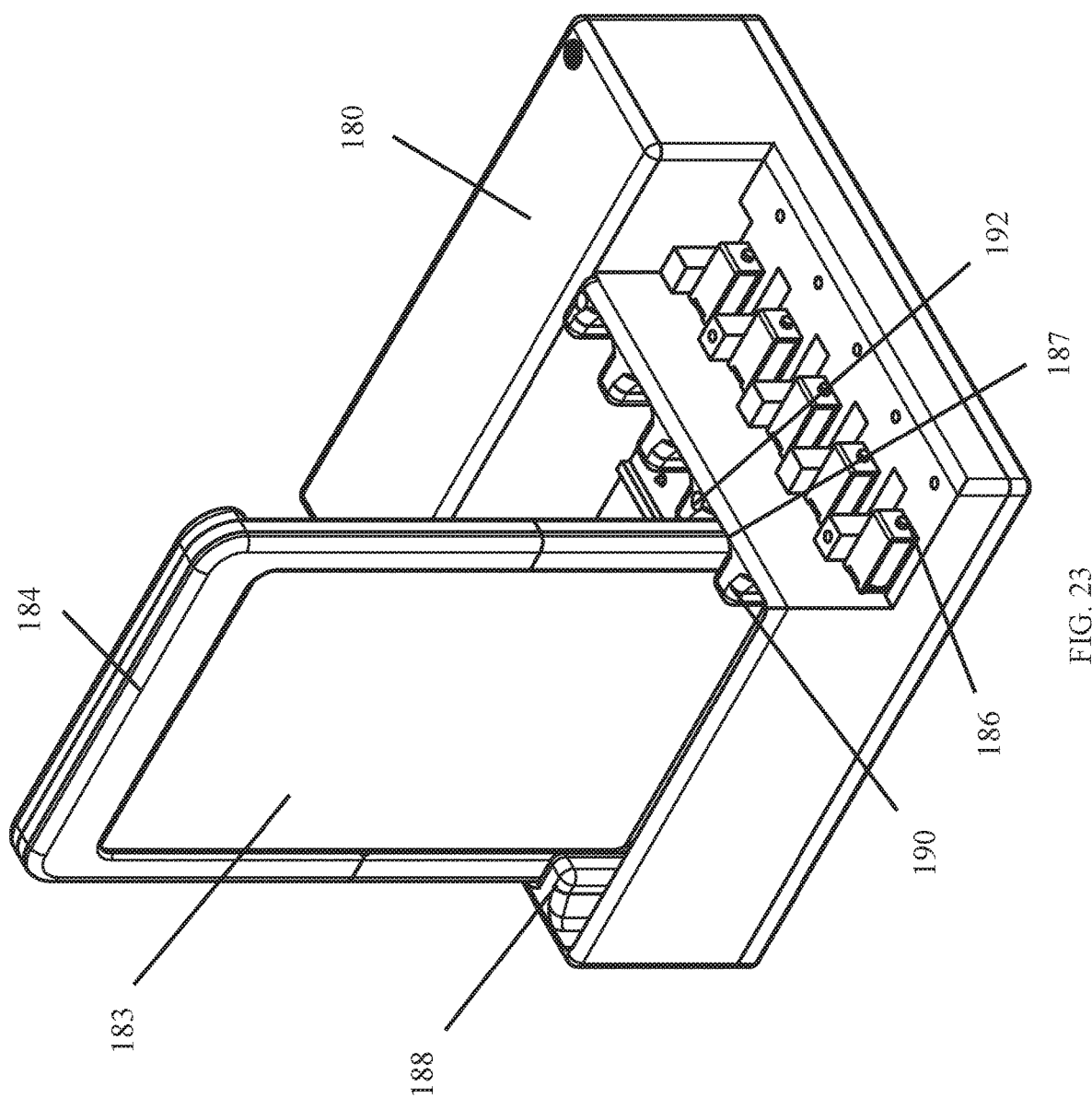
FIG. 23 is a perspective view thereof.
Figure 24:
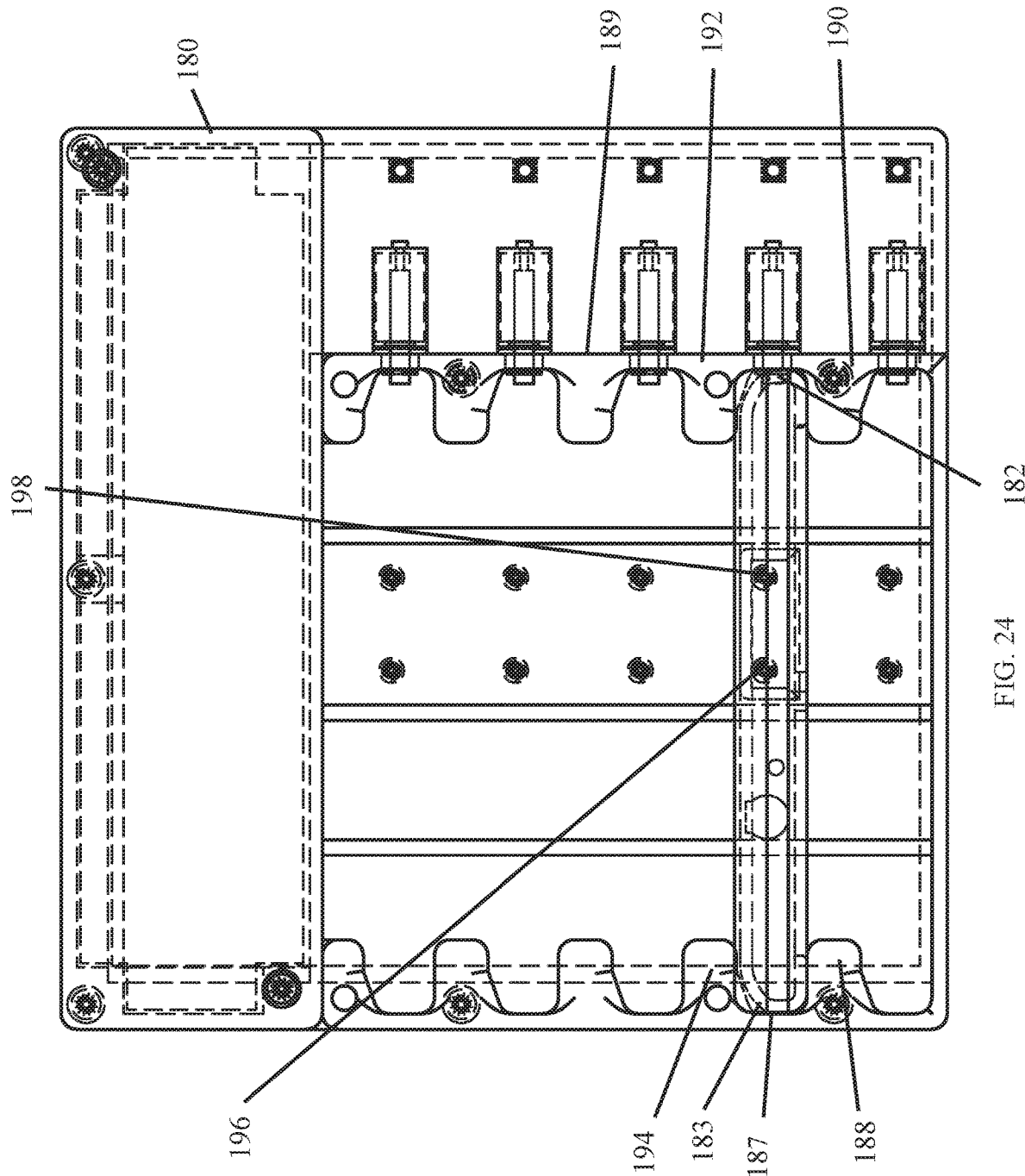
FIG. 24 is a partial view thereof.

FIGS. 23 and 24 show base 180 with device 183 and housing 184 inserted to receiving aperture 187 of base 180. The retention aperture 187 accepts insertion of the device 183 into the base 180 between retention arms 188, 190, 192, 194. The charging contacts 196, 198 located in retention aperture 187 charges the device. The retention apertures 187 and retention arms 188, 190, 192, 194 discussed in this embodiment may be similar to the retention apertures 112, 118 and retention arms 112, 114, 116, 118 discussed above.

The locking finger 182 adjusts between locked and unlocked. The locking finger 182 may be a solenoid, actuator, or other locking device. The locking finger 182 extends and retracts from a side wall 189. The locking finger 182 retracts within wall 189 to unlock the device. The locking finger 182 extends from wall 189 towards receiving aperture 187.

Figure 25:
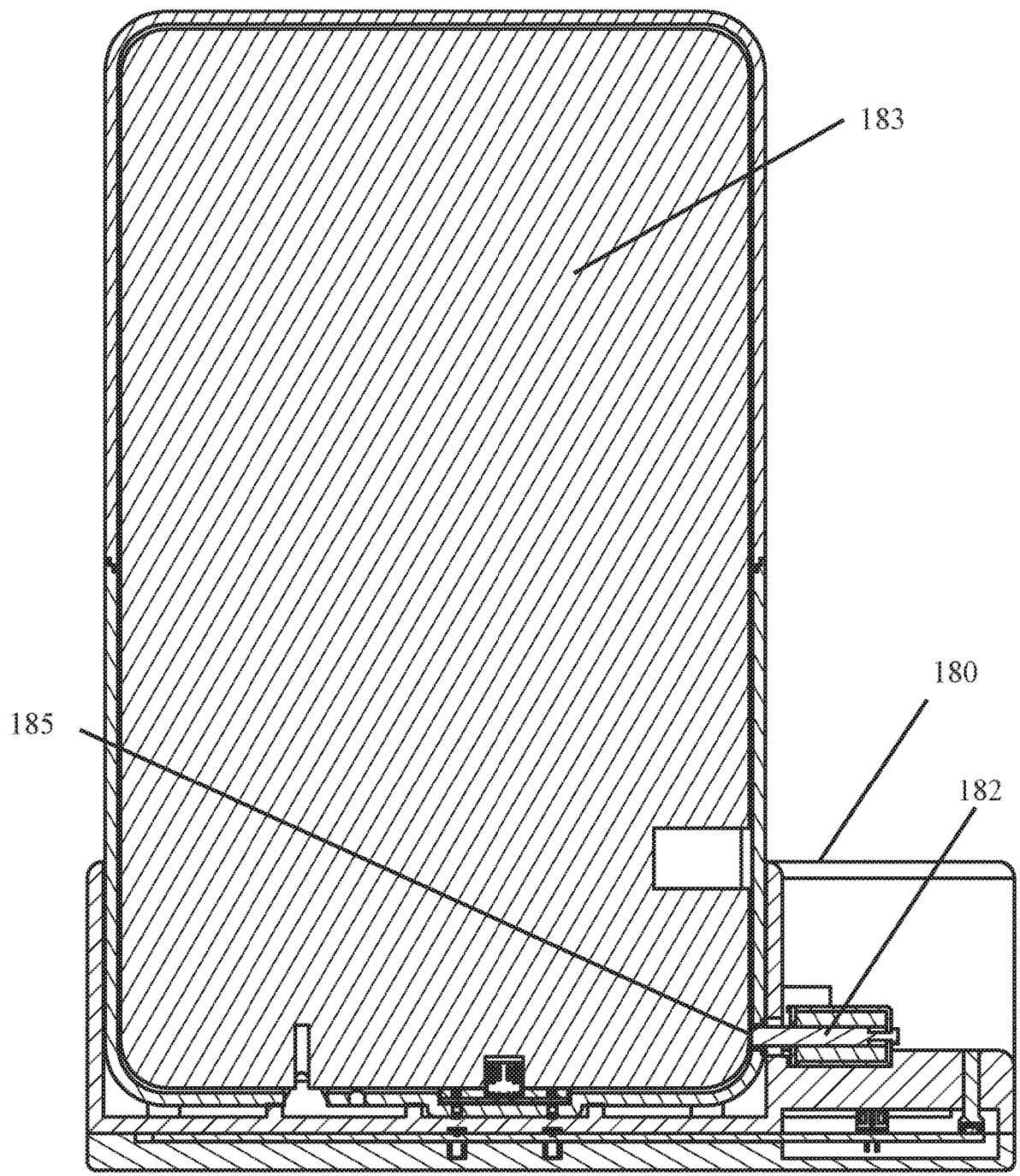
FIG. 25 is a partial view thereof.
Figure 26:
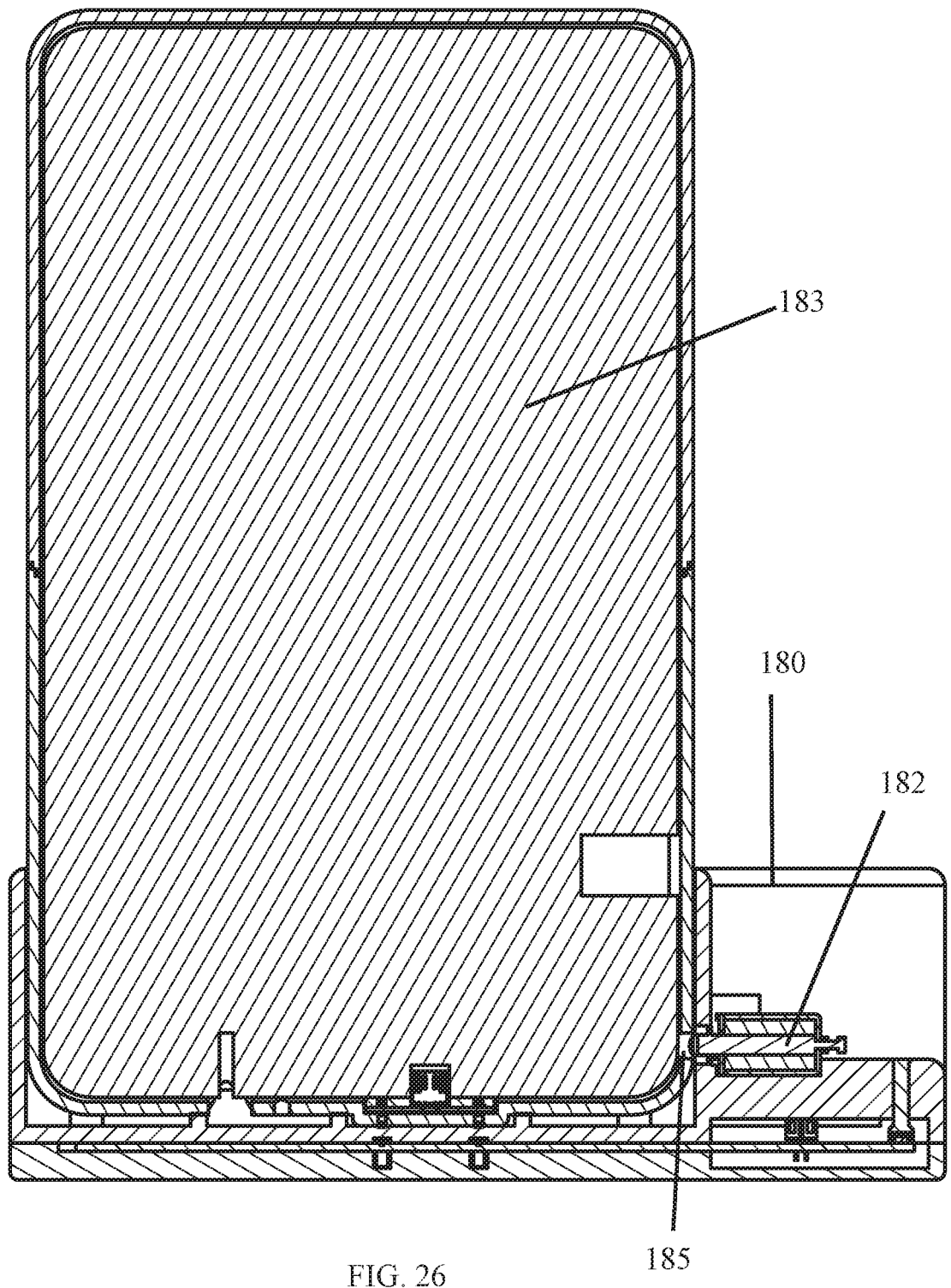
FIG. 26 is a partial view thereof.

FIGS. 25 and 26 show the device 183 secured within base 180. The locking finger 182 contacts the device 183 to secure the device 183 within the base 180. Such an embodiment enables the base 180 to secure devices 183 that are not stored within a case, such as housing 184. The locking finger of one embodiment inserts into the locking aperture 185 of device 183 to secure the device within the base. In another embodiment, the locking finger 182 inserts into locking aperture 185 of housing 184 and contacts device 183 to secure the device within base 180. The locking finger 182 of another embodiment may insert into locking aperture 185 of housing 184 such that the locking finger 182 is not required to contact device 183 to secure the device 183 within the base 180. Contact of the locking finger 182 with the device 183 or the housing 184 is sufficient to secure the device within the base.

FIG. 26 shows the locking finger 182 retracting to unlock the device. The locking finger 182 no longer contacts the device 183 or the housing 184. The locking finger 182 also retracts from locking aperture 185. The device 183 is no longer secured within base 180. The user can freely remove the device 183 from base 180.

The locking finger 182 has been described as contacting the device 183 or being inserted into locking aperture 185. The locking aperture 185 may be implemented in a case in which the electronic device 183 is inserted. In another embodiment, the locking aperture 185 may be implemented in device 183. Such a locking aperture secures the device when the locking finger inserts into locking aperture of either the device or a separate housing secured to the device.

Access to the device secured within the base may be granted upon certain conditions and/or rules. The system tracks usage of the devices and the status of the user. Such status of the user may be based upon the user's behavior, the user's prior usage of the device, and the user's position in the hierarchy of accessing a device. The server identifies which users should be granted access to the device. The server assigns a device to a user. The server transmits a message to the base identifying the device to be unlocked for the user. The server maintains a log of the devices that have been accessed by the users.

Figure 27:
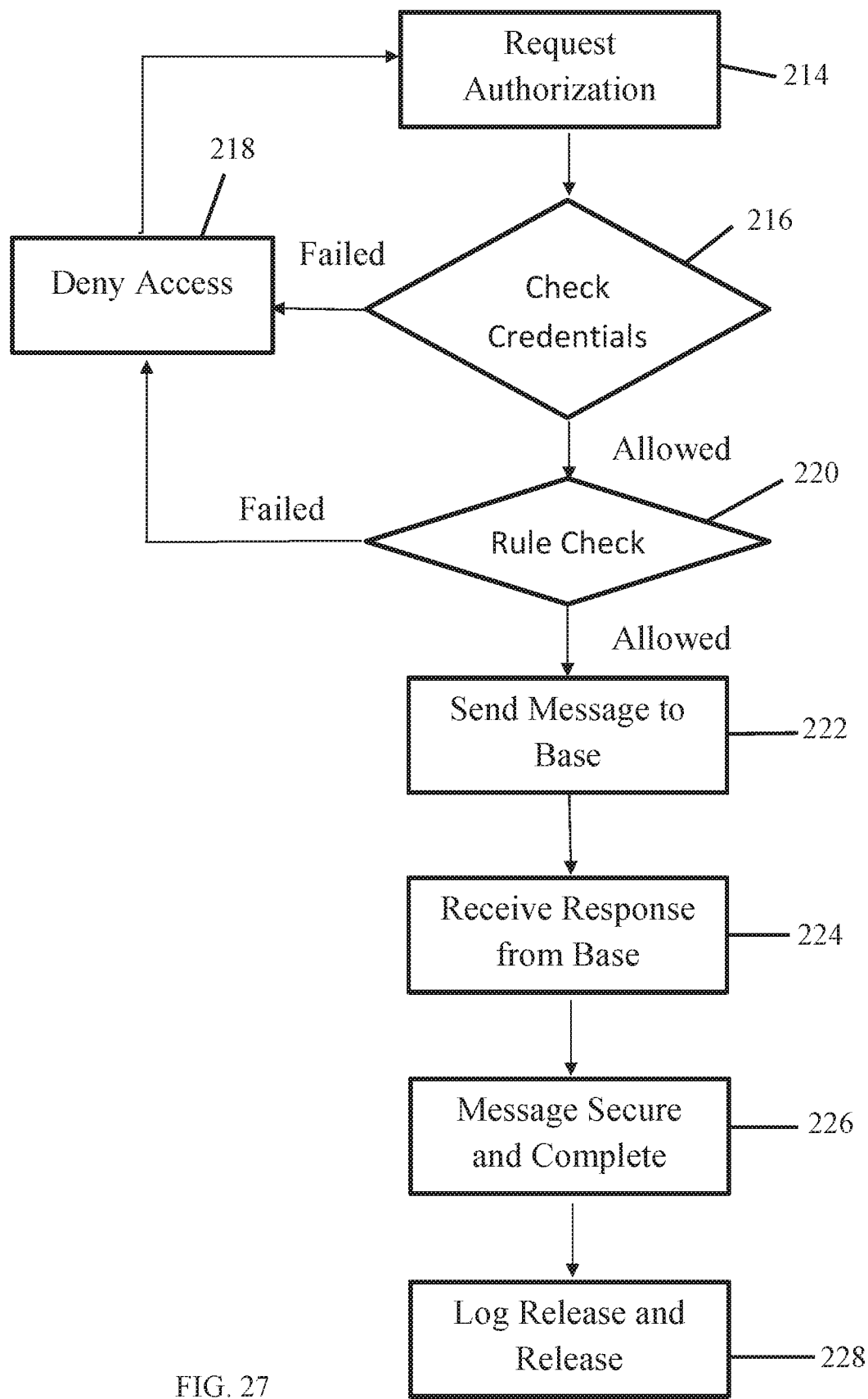
FIG. 27 is a flow chart view of one embodiment of the present invention.
Figure 28:
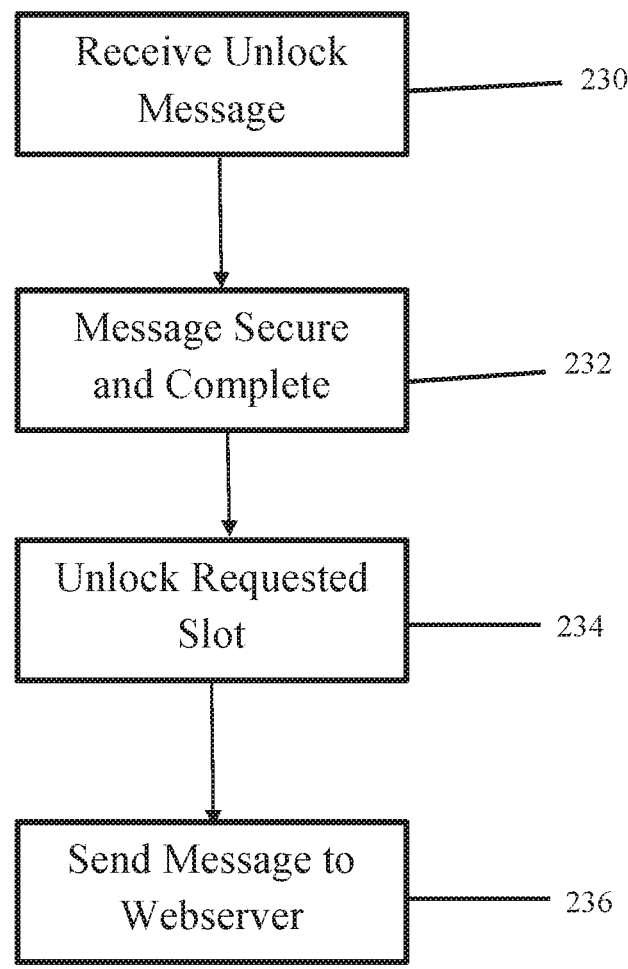
FIG. 28 is a flow chart view thereof.

To release a device from the base, a user must enter a proper authorization code as shown in FIGS. 27 and 28. FIG. 27 shows the processes occurring on the server to access the device. FIG. 28 shows the processes occurring on the base to access the device. The secured storage grants access to the user who provides the proper credentials and identification. The system includes a server, such as a computer or other computing device, in communication with the base. The system requests authorization from the user to access the device from secured storage at Request Authorization step 214. The user enters the user's identification and/or password to receive the device. The server authenticates the user's identification via such authentication methods which include, but are not limited to, password, PIN number, fingerprint, voice recognition, retinal scan, facial recognition, biometrics, or other authentication methods.

The server determines whether a proper identification has been entered at Check Credentials step 216. The server determines whether a proper user has attempted to access a secure device. If the credential check fails, the system denies the user access to a device at Deny Access 218. The system then requests authorization again at Request Authorization step 214. In one embodiment, the system may lock the user out by limiting the number of tries a user can attempt to access the device. The system may require the user to wait a specific amount of time before allowing the user to attempt unlocking the device.

If the user enters a proper identification, the server then determines whether the user should be allowed access to the device. The server checks the user and compares the user's identification against a set of rules or other criteria to determine if the system should allow the user access to a device at Rule Check 220. In one embodiment, the system compares the user's identification to an authorized list of users allowed access to the devices. The system defines rules determining whether to grant the user with access to a device. Such rules can include whether the device belongs to the user or whether the user should be granted access to a device.

The rules can include whether the device is sufficiently charged or in otherwise proper operating condition. The rules can define a minimum charge of the device. If the device is not charged to the minimum charge, the system denies access to the device. Such a charge may be based on the battery power of the device.

The rules may also be based upon rules or guidelines set forth by an institution, a school, a library, a prison, a jail, a detention center, a learning center, a business, a place of learning, or a place of confinement. The system may allow access to the device to users with good behavior, users who have time remaining to access a device, users who have not abused the devices, users who have not damaged devices, users who have not lost or stolen devices, users who have returned devices, or users who have not otherwise abused the system. The system may prevent access to the devices to those users who have poor behavior, users who have no remaining access time for a device, users who have abused the devices, users who have lost or stolen devices, users who have not returned devices, or users who have otherwise abused the system. The system may also deny access to the devices if insufficient devices remain and a user placed higher in the hierarchy is also attempting to access a device.

The system may deny access if a user has exceeded an available access limit. The system defines a set amount of time for which the user can access the device. The system tracks the amount of time a user has accessed the device from the base. If the user exceeds the available access limit, the server denies access to the device. The server confirms that the user has available access time remaining before releasing the device to the user.

The system may also restrict access to certain time periods. If a user attempts to access a device outside of the available access time, the system denies access to the device. The system will allow access to the devices if the user accesses the device during the available access times.

One embodiment of the present invention provides devices with specific features or limited capabilities. These devices are assigned a specific class. The system grants access to users to devices of a specific class. These classed devices may be restricted for access by only a few users, granted greater access to allow an increased number of users to access devices of the class, or provided for free or low cost. Such classes may be a library class device or communication class device. The server communicates with the base to identify which devices of a particular class that the user may access. The server identifies the user to determine the type of user. The type of user can access devices of a particular class or classes. The server identifies which classes the user may access and grants the appropriate access. The server instructs the base to release a device to which the user has proper access.

The library class may be provided for an inmate law library. Such a library class may be restricted to only a set of users such that users outside of that set cannot access devices in the library class.

The communication class provides a number of devices that are restricted to a more restricted set of inmates. User outside of the communication class cannot access the devices in the communication class.

At Rule Check 220, the system determines whether the user is approved to access a device. If the rules indicate that a user should not be allowed access, the system denies the user access to a device at Deny Access 218. The system then requests authorization from a different user at Request Authorization 214. As discussed above, the system may require the user to wait a specific amount of time before allowing the user to attempt unlocking the device.

The server of one embodiment implements the rules. If the server restricts a user from accessing a device, the server instructs the base not to release the device. The server sends the message to the base. The base then refuses access to the device. The base does not unlock the device. The locking finger remains to prevent the user from accessing the device.

If the user is allowed access at Rule Check 220, the system sends a message to the base indicating that the user is granted access to the base at Send Message to Base 222. The message includes an authorization for the user to access a device. In one embodiment, the message identifies a device that is assigned to the user. The message may include the identification of the slot in which the assigned device is stored. The base may then unlock the slot for accessing the assigned device.

The base then sends the system a message indicating that the base has received the message from the system. The message includes confirmation receipt of the message from the server. The message also includes confirmation that the base will unlock a device located at an identified slot.

At Message Secure and Complete 226, the server has received the message from the base. The server confirms the authenticity of the message from the base. The server also confirms that the authentic message is the complete message from the base. The server logs release information concerning the unlocked device at Log Release and Release 228. The information includes the user who accessed the device, the device ID assigned to the user, and the time that the device was released from the base. Such information allows administrators, staff, or others to identify which devices have been released. The server logs the identification of device and the identification of the user who accessed the device from the base. Such information enables the system to account for which users last accessed a particular device. The institution may then hold users accountable for devices accessed by the users.

Referring to FIG. 28, the base proceeds through the process of unlocking a device for access by the user. The base receives an unlock message from the server at the Receive Unlock Message 230. At Message Secure and Complete 232, the base confirms the authenticity of the message from the server. The base also confirms that the message from the server is complete. If the base confirms that the message from the server is complete and authentic, the base proceeds with unlocking the device. The base unlocks the device at the requested slot, such as a receiving aperture, at Unlock Requested Slot 234.

The base unlocks the device identified by the server. In another embodiment, the base may assign the device to be unlocked and transmits the device identifier associated with the device so that the server can log the device identifier and the user who accessed the device.

The base unlocks the device assigned to the user. The locking finger retracts to unlock the device. The user then removes the unlocked device from the identified slot of the base.

In one embodiment, the system may activate the screen of the device assigned to the user to allow the user to identify the unlocked device. In another embodiment, the system may display a message on the unlocked device assigned to the user. In another embodiment, the system may display a message on the devices for which the user is not granted access. In one embodiment, the system may simply display a message on the most visible device, such as the device placed in the most front position.

The retention fingers 188, 190, 192, 194 may be keyed to align the locking aperture 185 with the locking finger. Such alignment enables the insertion of the device into the base in the proper orientation for securing the device within the base. The keyed retention fingers with the locking finger reduce the possibility that the device may be inserted into the base improperly. The keyed retention fingers increase the likelihood that the device will be properly secured within the base.

The base of one embodiment restricts access of the device to authorized users and charges the device. The base provides charging apertures for receiving the mobile devices. A charger 121 is associated with each charging aperture 122 for charging the mobile device inserted into the charging aperture as shown in FIG. 1. The base controls each charger individually to allow selective charging of individual devices. For example, the server may determine that some devices should charge, and other devices not charge. The base then activates the chargers associated with the devices to be charged. The base does not activate the chargers associated with the devices not to be charged.

Figure 29:
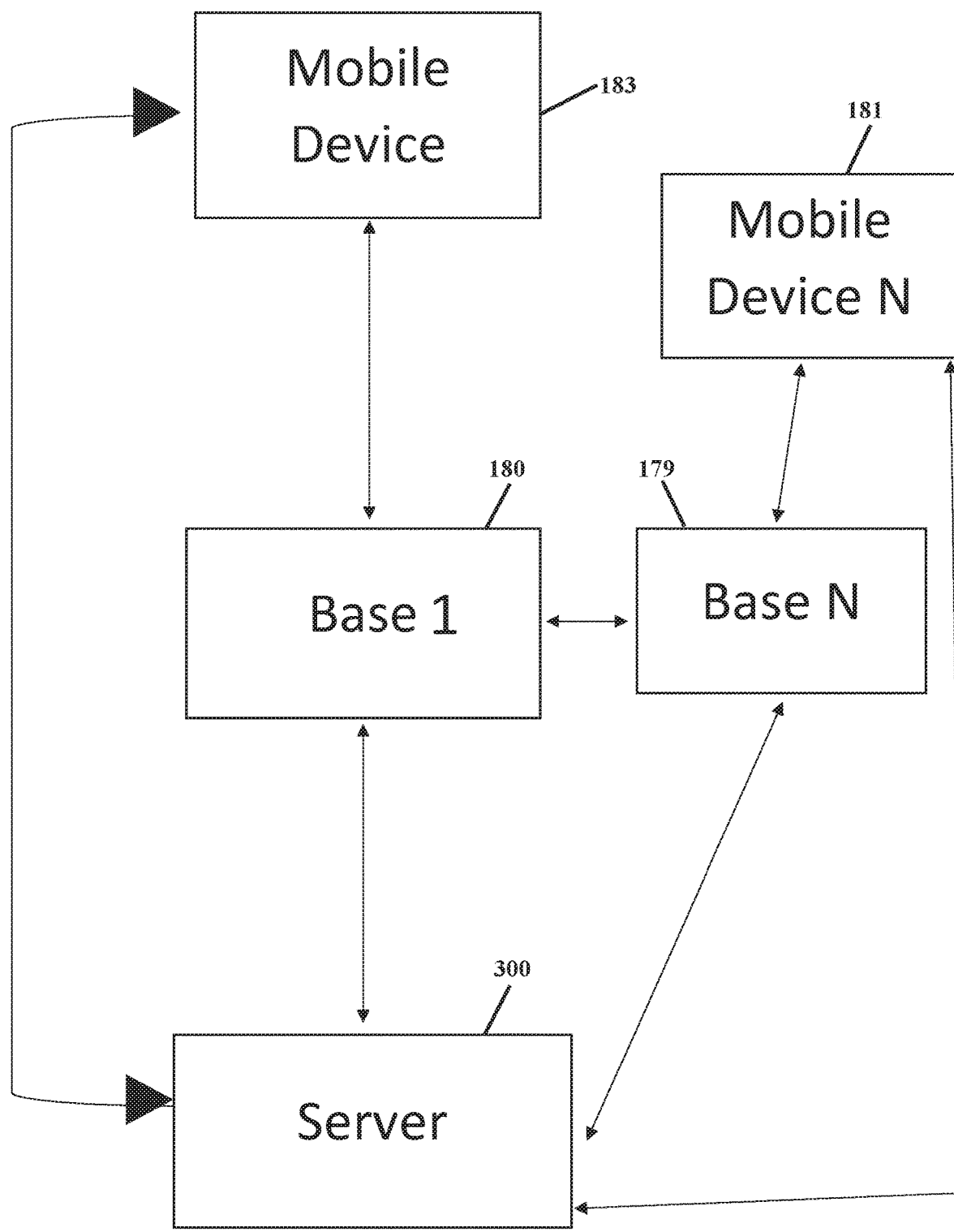
FIG. 29 is an environmental view of one embodiment of the present invention.

One embodiment of the present invention as shown in FIG. 29 provides a server 300 that controls the locking and unlocking of a mobile device 183 or multiple mobile devices 181, 183. The server 300 also controls the charging of the mobile devices by activating the chargers to charge selected devices. The mobile device 183 communicates with both the base 180 and server 300. The base 180 also communicates with both the mobile device 183 and the server 300.

FIG. 29 shows one embodiment of the present invention that provides multiple bases 179, 180. Mobile device 183 inserts into base 180. Mobile device 181 inserts into base 179. The mobile devices 181, 183 of one embodiment are not restricted to a base. Device 183 can insert and communicate with base 179 for identification, updates, upgrades, and other modifications as discussed below. Similarly, device 181 can insert and communicate with base 180 for identification, updates, upgrades, and other modifications as discussed below.

Bases 179, 180 and any other bases of the system can communicate with each other and the server 300. These bases can update, upgrade, or otherwise modify devices inserted into the base. The bases can identify the device identifiers of the devices that are inserted within the bases. The bases can communicate with each other and the server to identify the location of the devices and the devices inserted into each base. The server can then control charging of the different devices, cease charging through a designated base, etc. The bases may be placed in different areas of the facility. The server can then specify the different chargers to activate to charge the devices based upon the location of the base.

The bases identify the different devices inserted within each base. The bases report the devices within each base to the server. With such information, the server generates reports identifying the location of the devices, the user identifier of the user who accessed the device, the time of accessing the device, the time of returning the device, and the condition of the device.

Figure 30:
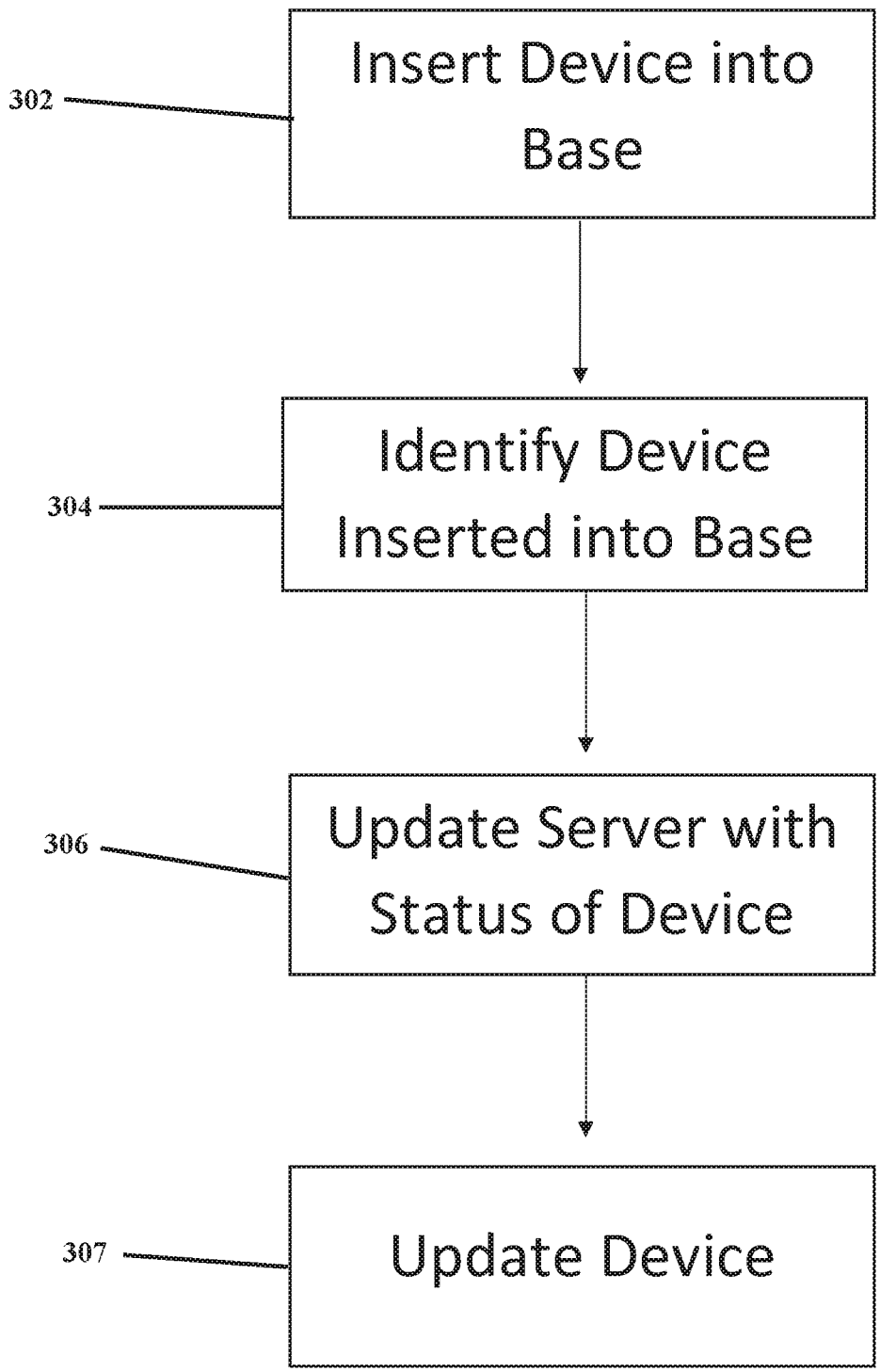
FIG. 30 is a flow chart view of one embodiment of the present invention.

FIG. 30 shows the process of the base identifying the device. The base 180 identifies the mobile device 183 inserted into the base 180 at insertion step 302. The secure charging base 180 identifies the mobile electronic device 183 via a unique device identifier associated with each device 183 at identification step 304. Such device identifiers include but are not limited to a visual indicator, such as a barcode or other visually detected identifier, or an electronic identifier assigned to the device that is accessed from the device 183. An identification system detects the device identifiers to determine the identification of the device. The identification system may determine the device identifier via a visual identification device, an electronic identification device, a reader, a communication system between the base and the device, or other detection system that can determine the device identifiers.

The electronic device 183 exchanges identification data with the base 180. Such identification may be detected by the base 180 with a visual identification device, including but not limited to a camera, a bar code reader reading a bar code or other identifier on the device, or other visual ID reader. Such visual identification device may be installed on the base.

In one embodiment, the device 183 exchanges the identification data with the base 180 through a communication system. The identification data transfers through a communication system, such as a wireless connection, a wired connection, Bluetooth communication, ultrasonic, light, light pulses, or a contact such as the charging contact or data contact. Other data may also be exchanged through such a communication system. Such data may include software upgrades, configuration profiles, charging profiles, updates, upgrades, and other data.

Upon identifying the device 183, the base 180 communicates with a central server 300 at update server step 306. The base 180 submits the identification data of the device 183, such as the device identifier, to the server 300. The base 180 of one embodiment of the present invention also identifies the base identifier associated with the base 180 and the aperture identifier of the charging aperture 122 at which the device 183 is installed for charging.

The server 300 may then maintain records of each device that is placed within a base 180 and the charging aperture and charger at which the device is installed. The base 180 then controls charging of the device. Such a base 180 enables controlled charging of the device even if the device is not connected via the network.

Upon insertion of the device 183 into a charging aperture, the base 180 transmits a charger request to the server 300 to determine if the base 180 should charge the device 183. The charger request provides sufficient information to the server 300 to identify the base 180 at which the device 183 is installed, the identifier of the device, and the identifier of the charger that will be charging the device.

In one embodiment, the base updates the mobile computing devices that have been inserted into the base as shown at Update Device Step 307. The device may not always be connected to a network to receive updates. Updating the computing device via the base avoids issues related to being disconnected from the network. The base receives the updates from the server. The communication system transfers data between the base and the device. As discussed above, the communication system transfers data through a physical connection, a wired connection, or a wireless connection.

The base then updates the device when the device is inserted into the base. The base may receive software upgrades, configuration messages that update configuration profiles for the devices, messages that update the charging profile, and other upgrades, updates, and/or modifications for the devices. The communication system transfers the data from the base to the device. The device may then communicate with the base to indicate that the device has been properly updated and/or modified. The base may then inform the server of the update and/or modification. One embodiment of the server updates the devices based upon the identity of the device and/or predefined rules.

Figure 31:
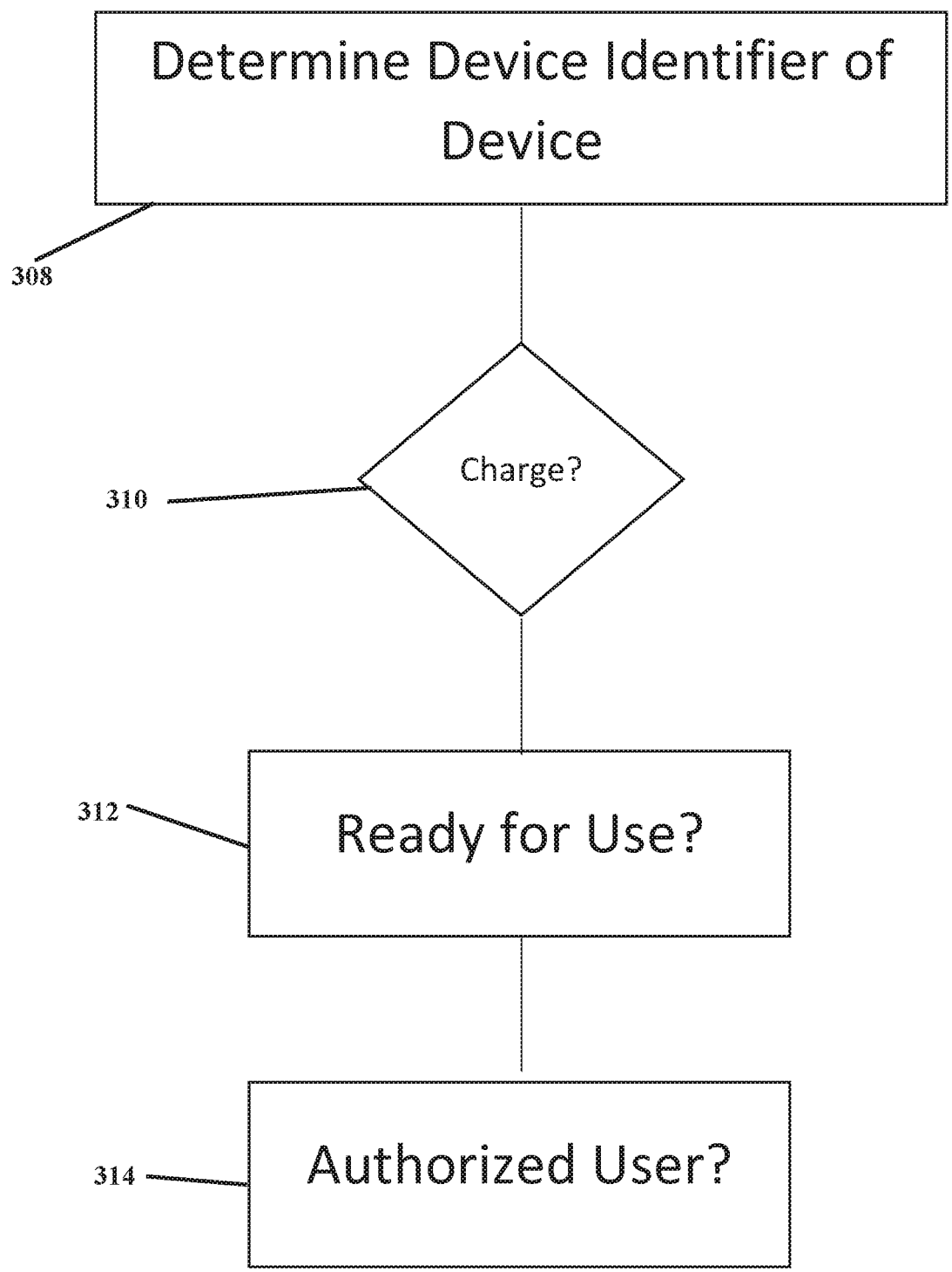
FIG. 31 is a flow chart view of one embodiment of the present invention.

FIG. 31 shows the process of charging the mobile computing device. In one embodiment, the base 180 selectively charges devices 183. The server instructs the base to charge specific devices. The base determines the identification of each device inserted into the base as discussed above in FIG. 30.

The server determines the identification of the device at Step 308. The server receives identification information from the device sufficient to determine the location of the device, the device identifier, the charging aperture at which the device is inserted, and the charging contacts that will charge the device.

After the server 300 receives the identification information with the charger request, such as the base identifier, the device identifier, the aperture identifier, and the charging contacts that will charge the device, the central server 300 compares the secure charger request against charging rules which apply to the specific mobile electronic device 183 at Charge Query 310. The rules may vary according to the needs of the controlled environment or facility. In one embodiment, the rules are stored within a database. The rules may be stored locally or remotely within storage. If the rules are met, the central server 300 instructs the secure charger to charge the device 183.

Once the secure charger receives authorization from the central server, the charger activates to charge the mobile device. Electricity flows through the charging conductors between the secure charger and the mobile electronic device for charging the mobile electronic device's battery.

Controlling the charging of the devices enables administrators to control usage of the devices that may not be connected to a network. Administrators may selectively charge devices to control usage of the devices. Without a charge, users cannot use or misuse the devices. Administrators simply stop charging selected devices to limit use of the device. If the unauthorized devices cannot be charged, usage of the unauthorized devices will eventually cease.

Figure 32:
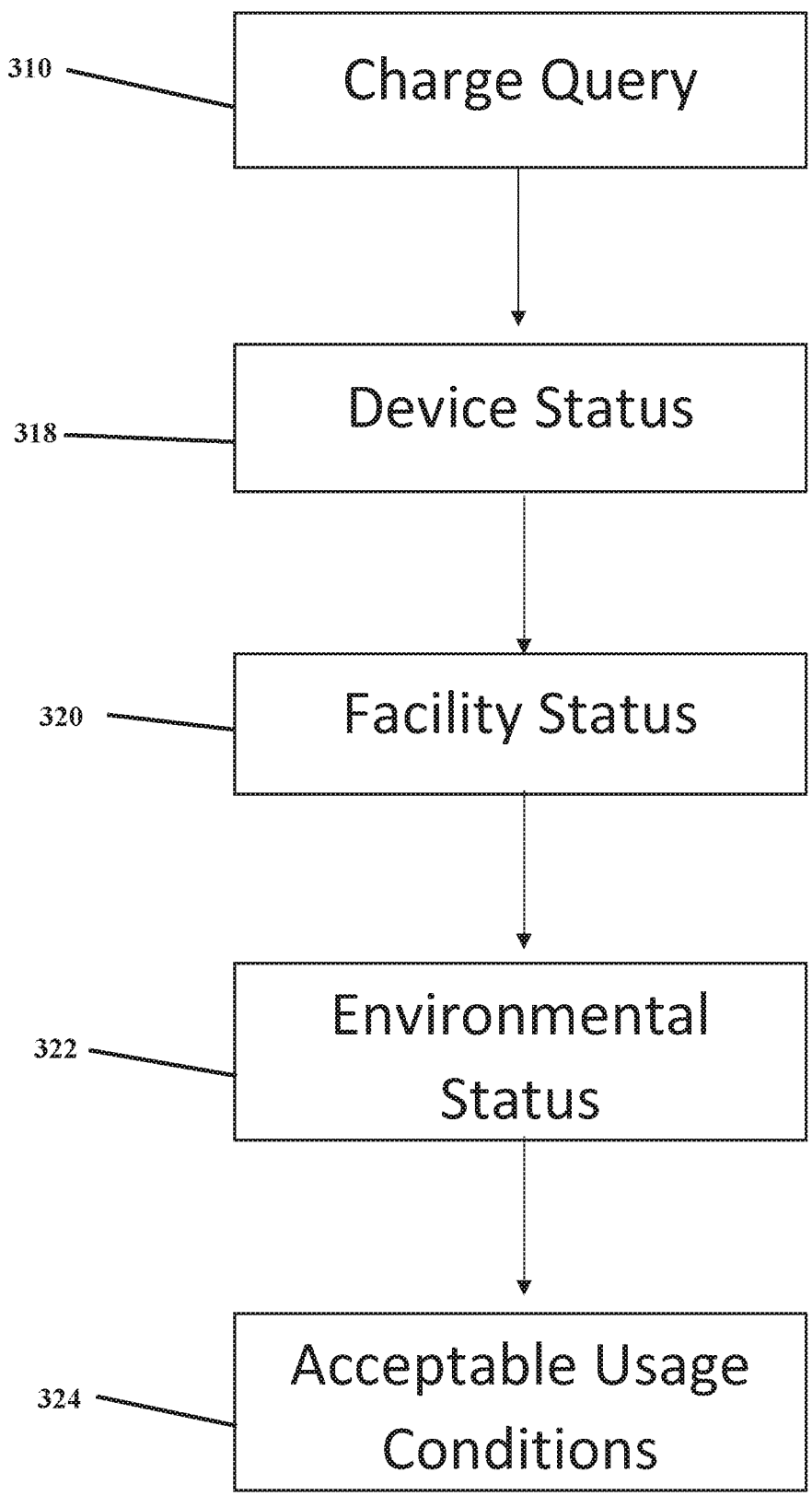
FIG. 32 is a flow chart view of one embodiment of the present invention.

The server may impose rules before charging the device. Such charging rules as shown in FIG. 32 consider the status of the device at Device Status 318, the status of the facility at Facility Status 320, the environmental status at Environment Status 322, the user's usage of the device at Acceptable Usage Condition 324, and other conditions.

The server and/or the base may determine that a device has been damaged or otherwise tampered with. If such a device has been damaged or tampered with, the server instructs the base not to charge such a device. The base may identify damaged devices based upon a visual inspection via the camera.

The base may also identify damaged and/or tampered devices by identifying devices that no longer properly fit within the base. Such proper fit may be determined by the base's ability to lock the device within the base. If the lock cannot properly secure the device within the base, the device has been tampered with or damaged. The base will not charge such a device.

The base may identify which locks have not been fully adjusted to the locked position. The base will then not charge those devices that are not fully locked if such a charging rule is implemented.

Other rules may be directed to the facility status. Such rules may require proper operation conditions to be in place to allow charging. The base may prevent charging of the devices in riot situations, emergency situations, lock downs, or other unsafe conditions. During such situations, the server transmits a facility cease charging command that disables the bases' charging capabilities. The administrators may override the facility cease charging command. The bases may be installed in different areas such that the cease charging commands can disable only the bases within a designated area. The cease charging command may be sent to only those bases in the defined zone to be disabled.

Other charging rules implemented by the server include battery condition rules. Such battery condition rules include stop charging if the temperature within the base is above a designated temperature, such as 113° F. Avoiding charging at such temperatures prolongs battery life of the device. The base transmits the temperature at the base to the server for the server to implement the charging rules.

The battery condition rules may also enable or disable charging based upon the charging profile of the battery. If the charger determines an improper charging profile of the battery, the base may slow charging or disable charging of the device. In most instances, the base will slow charging to prolong battery life.

The charger may also determine if a battery is not sufficiently charged. In some instances, a device may be returned to the charger with insufficient charge for operation of the device. The charger will then charge the device with enough electricity to identify the device. If an acceptable device identifier is not determined by the time a sufficient charge is acquired by the device or by a predetermined time, the charger will no longer charge the device. Such a charging system eliminates charging of unauthorized devices.

In some embodiments, an administrator inputs charging rules into a central server database using a web form, specifying a rule defining what devices are allowed to charge, the times charging is allowed, and which users are allowed to unlock the mobile electronic device from the secure charger. Upon request by the secure charger, the central server uses the predefined rules setup by the administrator to determine whether the mobile electronic device should be charged while connected to the secure charger. In this embodiment, the central server also authenticates end users requesting the release of a mobile electronic device locked in the secure charger and determines whether to unlock the mobile electronic device based on the rules established by the administrator.

The server determines that the rules are met to enable charging of the device. The base charges the device until the device is ready for use. After the device is sufficiently charged, the device enters the rotation to be checked out to authorized users at Ready for Use query 312. An authorized user may then check out the device if the server and base authorize the user's use of the device at Authorized User query 314.

The base of one embodiment provides a base data contact within the charging apertures with the charging contacts as shown in FIGS. 35-38. The base data contact communicates with a device data contact. The base data contact and the device data contact transfer information between the device and the base. Such data transfer between the base and the device provides additional control of the devices.

The base of one embodiment identifies the device identifier associated with each device via the data contacts. Administrators can also update the devices as needed. The base transfers the data needed to update the device to the device via the device contacts as shown in FIGS. 35-38.

Figure 33:
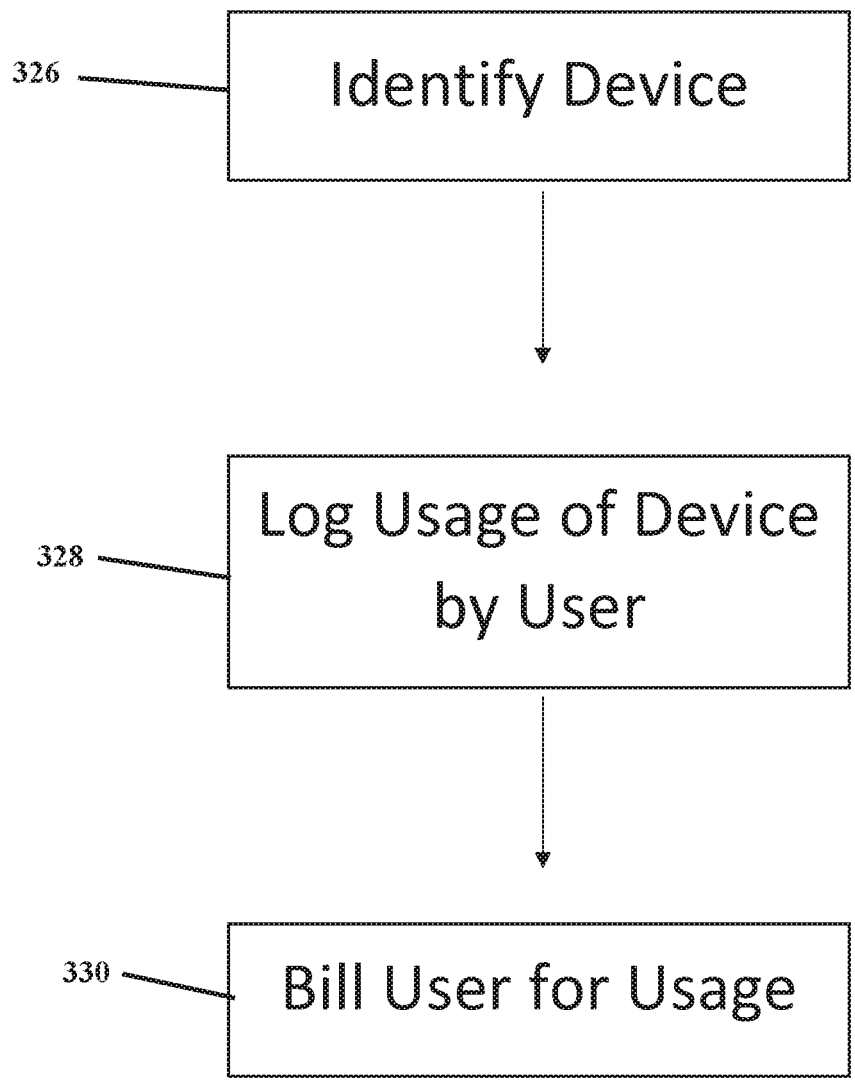
FIG. 33 is a flow chart view of one embodiment of the present invention.

The present invention also provides a billing system for billing the usage of the devices as shown in FIG. 33. The billing system bills the user and the user accounts associated with the users. The user checks out the device from the base. The server associates the user with the device to identify the user who has checked out the device for usage at Identify Device 326. The server logs the usage of the device by the user at Log Usage 328. Such logging may include a user identifier, a device identifier, and a time and date that the device was released to the user. The server may also log the condition of the device at the time that the device was released to the user. The server may also log the charge percentage of the battery of the device at the time the device is released to the user at Log Usage 328.

The user must then return the device to a base. The system will also log the return of the device. The system will log the condition of the device, the charge percentage of the battery of the device, and the date and time that the device is returned.

The system then bills the user for the usage of the device at Bill User 330. The system may bill based upon the time for which the device was released to the user. Such billing may be based upon the time that the user had the device. The system may also allow for a free period of time. The system grants access the user with access to the device for a limited time without charge. If the user exceeds the free time, the system allows continued access to the device with for a fee. The system bills the user/user account for the continued use of the device.

Such billing may be based upon the class of the device that the user accesses. Some classes of device may be provided at no charge or at a reduced rate. Other classes of devices may be provided to the user at an increased rate. For example, library class devices may be provided at no charge or billed at a lower rate. Devices in the entertainment class may be billed at a higher rate due to the increased features.

Another embodiment may bill the user based upon the power consumption of the device. The system determines the amount the battery has drained while the device is released to the user. The system may also bill upon the amount of electricity required for the device to be charged to the percentage at which the device was released to the user.

The system may also bill the user each time the user checks a device out from the base. Upon removing the device from the base, the base instructs the server that the device has been removed by a specific user. The billing system then bills the user/user's account for usage of the device due to the removal of the device from the base. In another embodiment, the user is billed upon the removal and return of the device to the base.

The system also generates alerts based upon predefined rules. The rules of one embodiment generates alerts based upon predefined rules stored in the server. Such rules generate an alert based upon:

a) Detection of lock not fully engaging the mobile device such that the device is not secured within the base;
b) Detection of a damaged device;
c) Detection of a device that has been tampered with;
d) Detection of a device with no power;
e) Detection of a device that requires a software upgrade;
f) Detection of a device requiring an updated configuration profile;
g) Detection of a device with an inadequate charging profile;
h) Detection of temperature exceeding a predetermined temperature;
i) Detection of removal of a device without authorization;
j) Detection that a device has not been removed from the base within a predefined time period;
k) Detection that a device has not been returned to a base within a predefined time period; and
l) Detection of an unauthorized device.

The system may generate an alert that is transmitted to the server. The server may then alert personnel of the alert condition that triggered the alert. Such an alert may be a message sent to a cell phone, a computer, a pager, or an audible alarm.

Another embodiment of the present invention provides an audible alarm. The alarm may be installed within a base or within the facility. The alarm of one embodiment activates if a device is removed without authorization. The alarm alerts the personnel that a device is removed without authorization. In another embodiment, the alarm may activate upon detection of the alert conditions identified above. The system indicates which condition triggered the audible alarm.

One issue in correctional facilities is that inmates tend to be possessive of a particular device. The inmate may intimidate, harass, threaten, or otherwise harm another person for using such a device. For this reason, a device may remain within a base. The server identifies mobile devices that have not been removed from the base for a predetermined amount of time. Such identification alerts the administration that a particular device has been claimed by an inmate such that no one will use the device. The facility may then remedy the situation by pulling the device from rotation or moving the device to an area not accessible the inmate claiming ownership.

The server also identifies the mobile electronic devices that have not been returned to the base within a predefined time period. The server alerts the administration that a mobile device has not been returned to the base within the time period. Because the server can communicate with multiple bases, the server can check the status of the devices within all of the bases of the facility. The server of one embodiment generates an alert or an alarm to indicate that the device has not been returned.

In one embodiment, the system deactivates a device that has not been returned to the base within the predefined time period. The server instructs the device to deactivate. The server of one embodiment denies the device access to the network. In another embodiment, the server sends the instruction to deactivate directly to the device. The device then deactivates until the administrator reactivates the device.

In one embodiment of the present invention, the server can identify the number of devices within the base(s) of the facility. The server can take an inventory to determine if any devices are not installed within the base(s). The server can then instruct the base to lock all devices within the base(s) until all of the devices are accounted for by being returned to the base(s). In one embodiment, the server requires a predefined number of devices to be inserted into the bases before unlocking any of the devices from the base. The system will allow an administrative override to allow administrators access to devices within base. The server instructs the bases to prevent access to the devices. The bases then lock the devices within the base.

Figure 34:
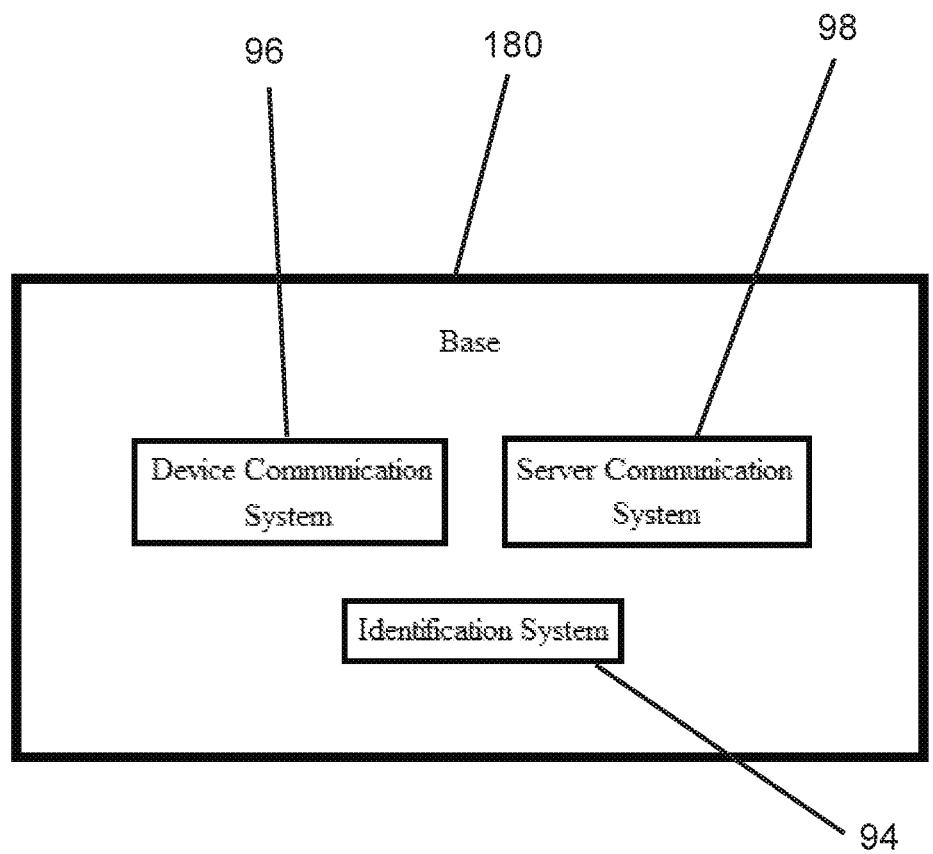
FIG. 34 is a schematic view of one embodiment of the present invention.
Figure 35:
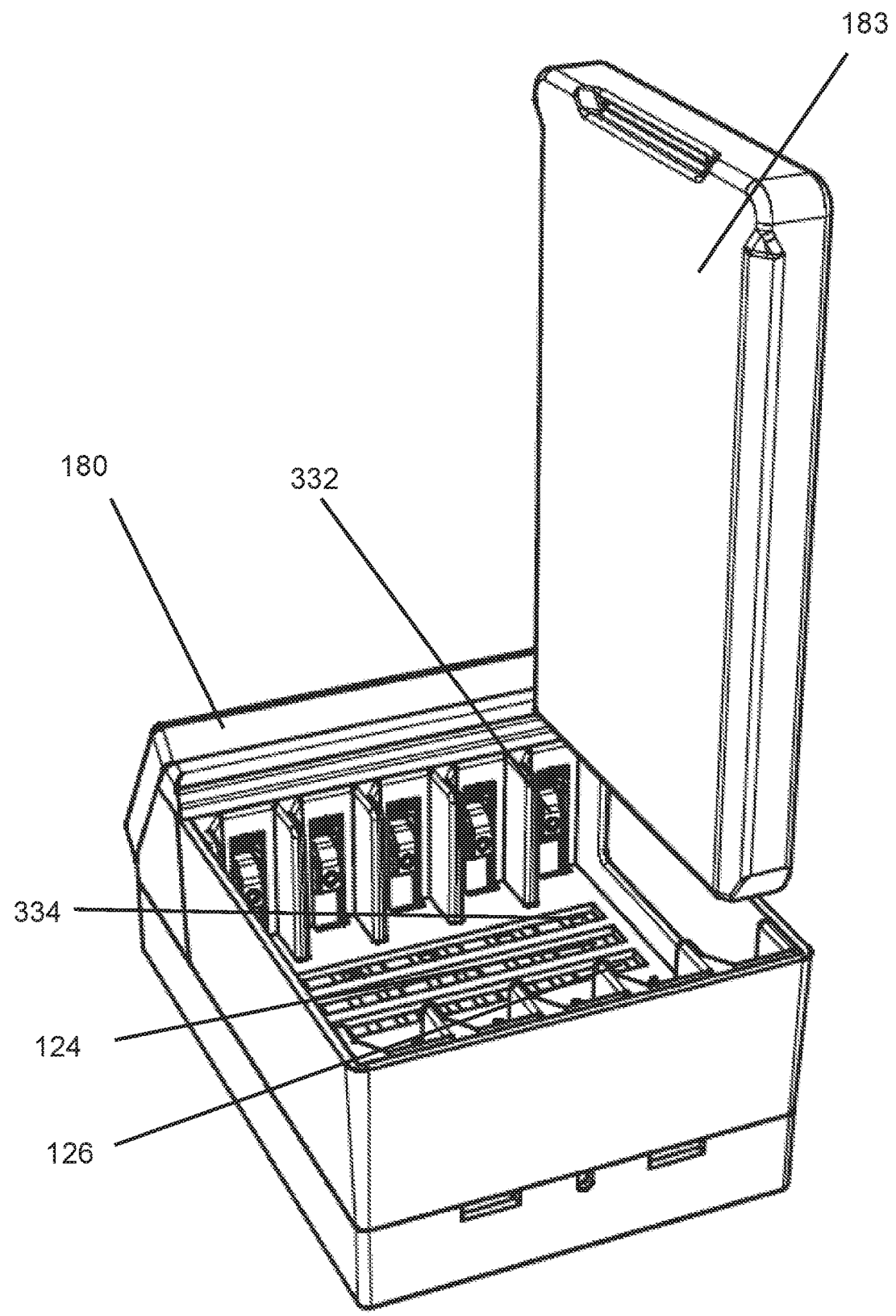
FIG. 35 is an environmental view of one embodiment of the present invention.

FIG. 34 shows a base 102 of one embodiment of the present invention. The base 102 provides an identification system 94 that communicates with the device to determine the device identifier of the device inserted into the base 102. The secure charging base 102 identifies the mobile electronic device via a unique device identifier associated with each device. Such device identifiers include but are not limited to a visual indicator, such as a barcode or other visually detected identifier, or an electronic identifier assigned to the device that is accessed from the device. An identification system 94 detects the device identifiers to determine the identification of the device. The identification system 94 may determine the device identifier via a visual identification device, an electronic identification device, a reader, a communication system between the base and the device, or other detection system that can determine the device identifiers.

The base 102 of one embodiment identifies the device with a visual identification device, including but not limited to a camera, a bar code reader reading a bar code or other identifier on the device, or other visual ID reader. Such visual identification device may be installed on the base.

The base 102 of another embodiment identifies the device through the device communication system 96. The identification data transfers through the device communication system 96, such as a wireless connection, a wired connection, Bluetooth communication, ultrasonic, light, light pulses, or a contact such as the charging contact or data contact.

The base 102 communicates with both the mobile computing device and the server. The device communication system 96 communicates between the mobile computing device and the base. The server communication system 98 communicates between the server and the base 102. Such communication transmits information and data between the mobile computing device and the server. Such communication informs the server of the devices within the base. Such communication also updates the computing devices with any updates, instructions, or modifications implemented by the server.

The device communication system 96 transfers data between the device and the base. Such data may be received from the server to be transferred from the base to the device. Such data may include software upgrades, configuration profiles, charging profiles, updates, upgrades, instructions, and other data. The device communication system 96 transfers data from the base to the mobile computing device. Such communication enables data transfer without connection of the device to a network. Data transfers between the base and the device via the device communications 96 which includes but is not limited to a wireless connection, a wired connection, Bluetooth communication, ultrasonic, light, light pulses, or a contact such as the charging contact or data contact.

As discussed above, the server transmits instructions for the device to the base. The base then relays these instructions to the device. Such instructions include but are not limited to updating the device, updating the charging profile, powering the device on, powering the device off, and disabling the device. The server identifies which devices require the instructions. The base delivers the instructions to the device. The base delivers the instructions to the devices via the device communication system. The server or the base can identify the devices to receive the instructions. In one embodiment, the base delivers the instructions via the data contacts.

In one embodiment, the server transmits the instruction to the base with the identity of the data contacts of the devices to receive the instruction. The base transmits the instructions to the identified devices via the data contacts. In another embodiment, the base identifies which devices receive the instruction and forwards the instructions.

For example, the server transmits a message to the server to power off a device or devices. The server identifies the devices to power off. The base then sends the instruction to the device to power off. The device then powers off. Similarly, the base can instruct devices to power on. The server identifies the devices to power on and sends the appropriate instructions.

The base 102 receives and transmits data to and from the server via the server communication system 98. Such a system may be a wired communication or a wireless communication. The base receives updates, modifications, or other changes from the server to implement on the mobile computing device. The base 102 transmits data to the server. Such data may include identification data of the devices within the base, a device profile of the devices stored in the device, user information identifying the user who accessed a device. The server communication system 98 updates the server with the information concerning the status of the devices and the location of the devices.

FIGS. 35-38 show an embodiment of the present invention that provides data contacts for communication between the base 180 and the mobile computing device 183.

FIGS. 35-38 show that a device 183 is placed within the base 180. The base 180 provides photoeyes 332 that detect the presence of a device 183 within the base 180. The photoeyes 332 inform the base that a device is present. The base 180 then identifies the device 183 via the communication system or the identification system. The base 180 then informs the server of the presence of the device 183 within the base.

Figure 36:
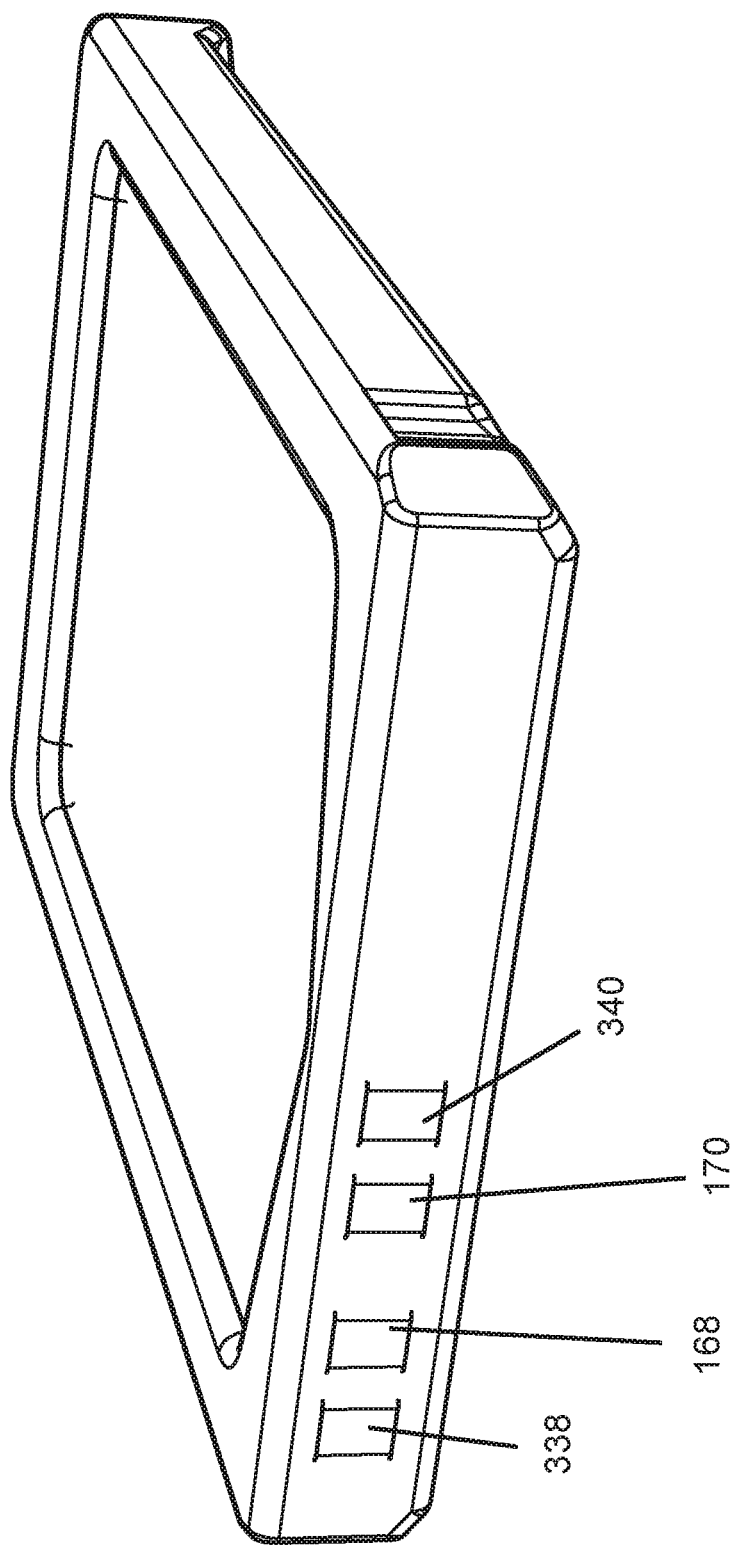
FIG. 36 is a perspective view of a mobile computing device and housing of one embodiment of the present invention.
Figure 37:
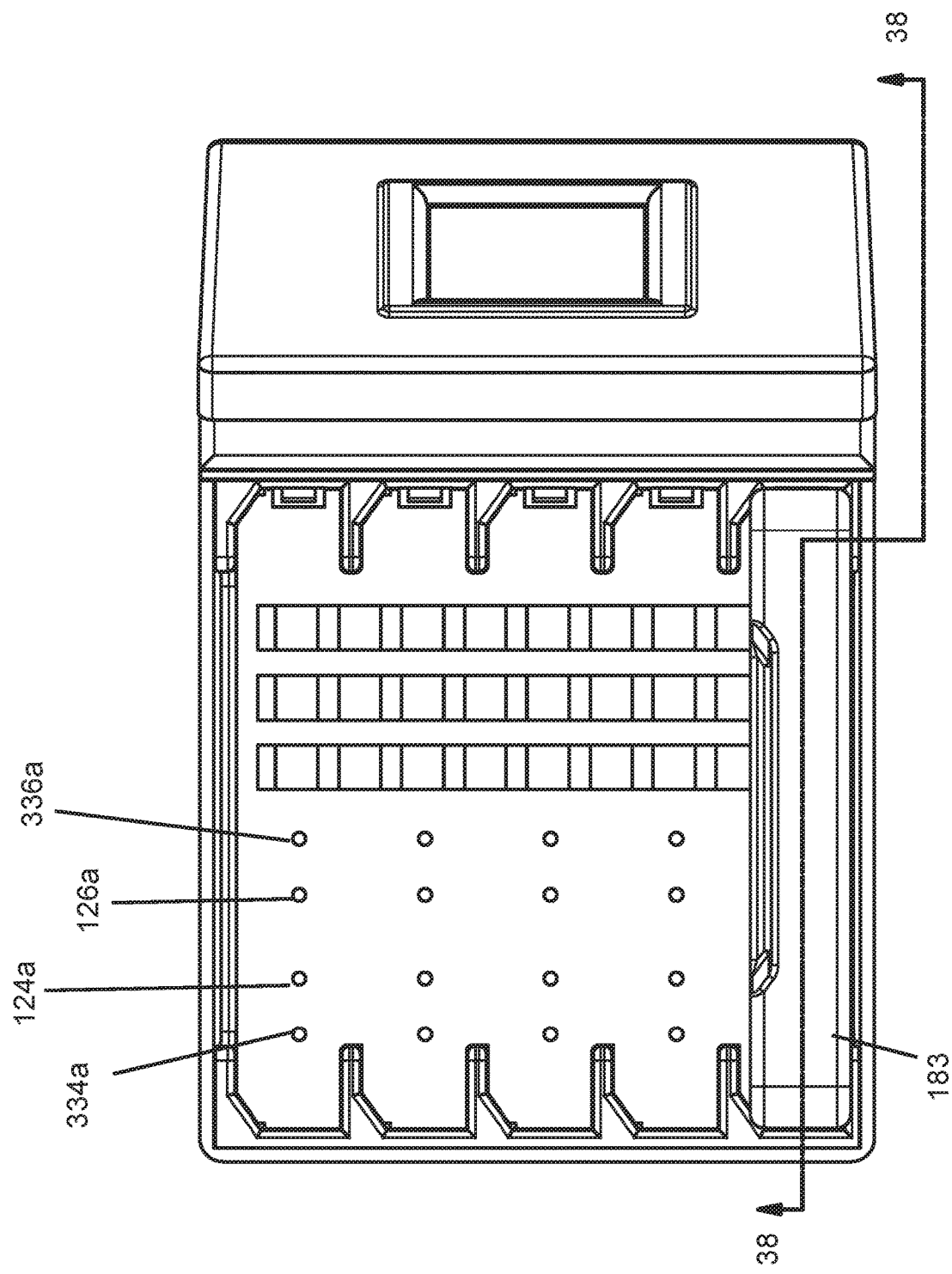
FIG. 37 is a top view of a base of one embodiment of the present invention.
Figure 38:
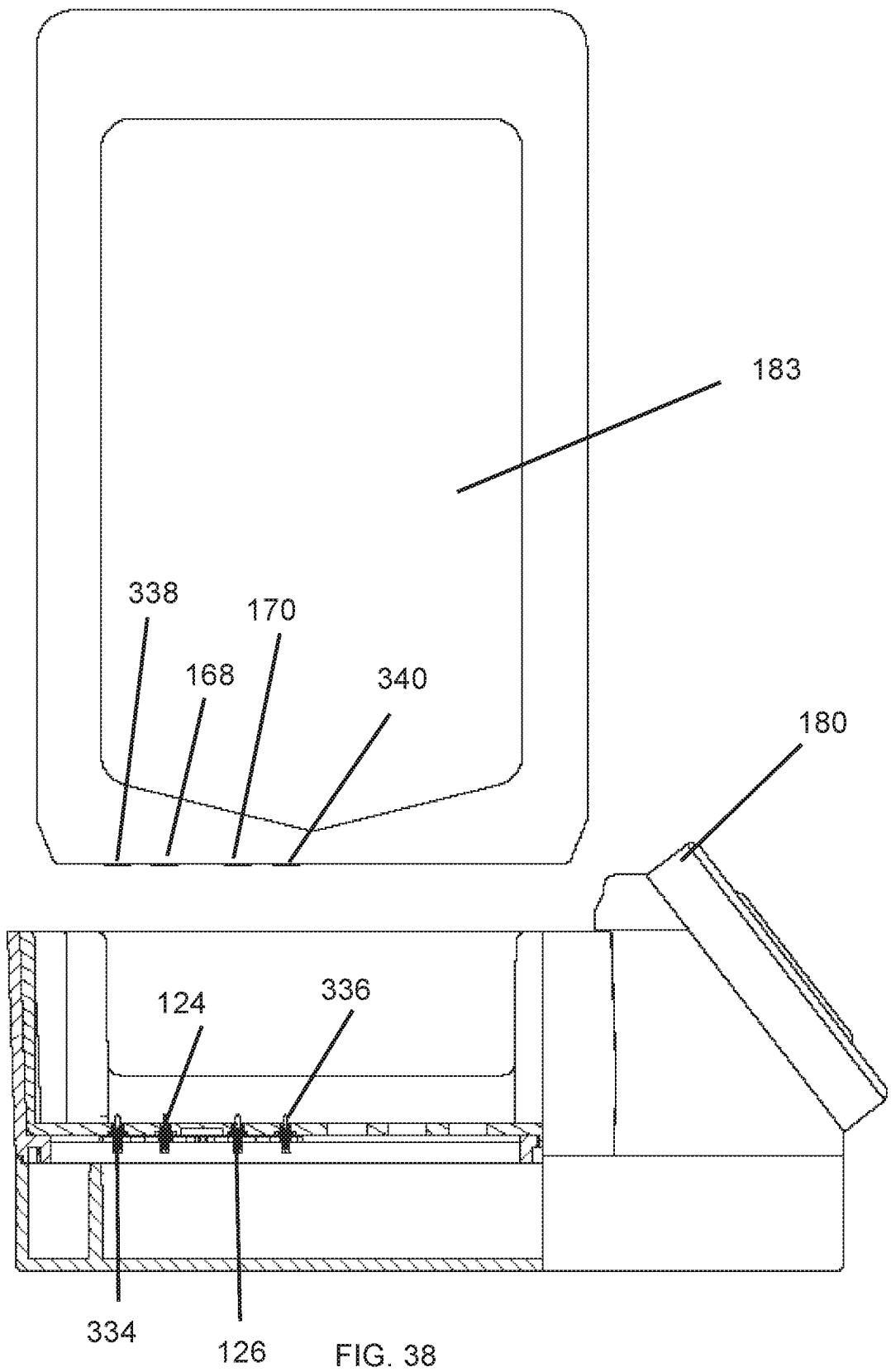
FIG. 38 is a sectional view of one embodiment of the present invention.

FIGS. 35-38 also show the charging contacts 124, 126 and the data contacts 334, 336. The charging contacts 124, 126 function as described above. The charging contacts 124, 126 of the base 180 contact charging contacts 168, 170 of the device 183 as shown in FIGS. 36 and 38.

FIGS. 35-38 also show the data contacts that transfer data between the base 180 and the device 183. The base 180 aligns the data contacts 334, 336 of the base 180 with the data contacts 338, 340 of the device 183 to contact each other. The communication system transfers data between the base 180 and the device 183 via the data contacts 334, 336, 338, 340 of one embodiment of the present invention.

The data contacts 334, 336, 338, 340 contact each other to transfer an electric signal between the device 183 and the base 180. The device data contacts 338, 340 of one embodiment connect to a port of the device 183. The data contacts 338, 340 contact a pin of the port to transfer data between the device and the base. In one embodiment, the data contacts 338, 340 are formed as part of the device. In another embodiment, the data contacts 338, 340 are implemented on the charging adapter similar to the charging contacts described above.

A port of the device provides different pins capable of different functions such as charging the battery and transferring data as shown in FIGS. 35-38. At least one of these pins, a communication pin, provides a communication path between the device and the base. In one embodiment, the charging adapter serves as the communication system capable of identifying the device. The charging adapter of one embodiment provides contacts, such as data contacts 338, 340, that communicate with the mobile device through the communication pins of the device. The data contact of the charging adapter contacts the communication pin of the mobile device. The communication system of one embodiment is implemented through the data contact.

The base of one embodiment communicates with the mobile device through data contact of the charging adapter and the communication pin of the device as shown in FIGS. 35-38. The base receives identification data from the device. The base determines the identification of the device. The server then instructs which devices to charge and which devices to release to specified users.

The charging contacts, data contacts, and orientations have been shown in one manner as shown in FIGS. 35-38. The placement of the charging contacts and data contacts may vary according to the placement of the port and the size of the station. The charging station may be configured to accept the electronic device in other orientations that will allow for charging of the device.

FIGS. 39-42 show the base 102 with the sanitizing system 350 installed within the charging apertures 122. The sanitizing system 350 sanitizes, cleans, and/or disinfects the electronic device 106. In one embodiment, the sanitizing system 350 cleans the electronic device prior to releasing the device to an authenticated user. The sanitizing system may be implemented on the rules based system described above that applies rules to determine if the device should be released to the authenticated user.

Figure 39:
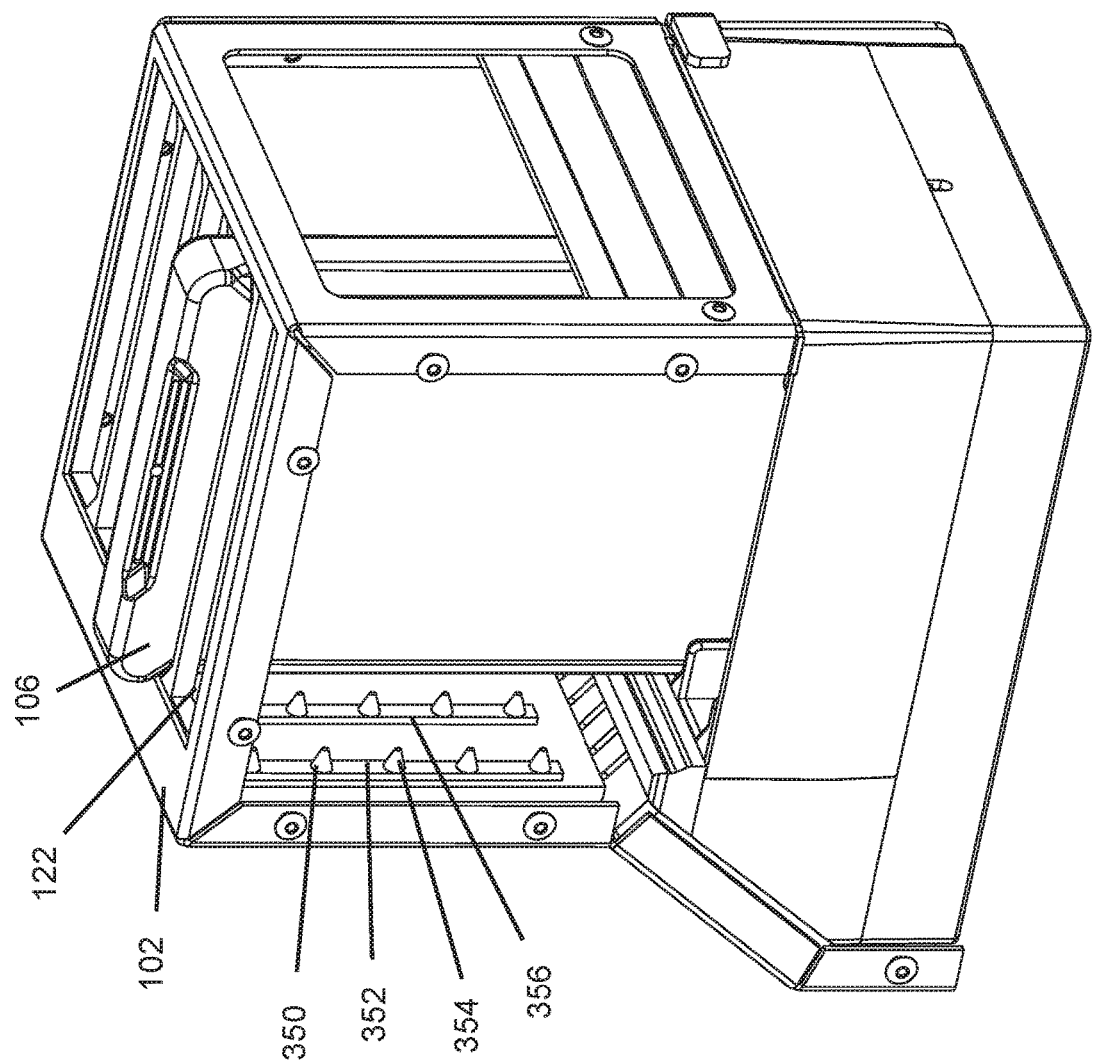
FIG. 39 is a perspective view of one embodiment of the present invention.
Figure 40:
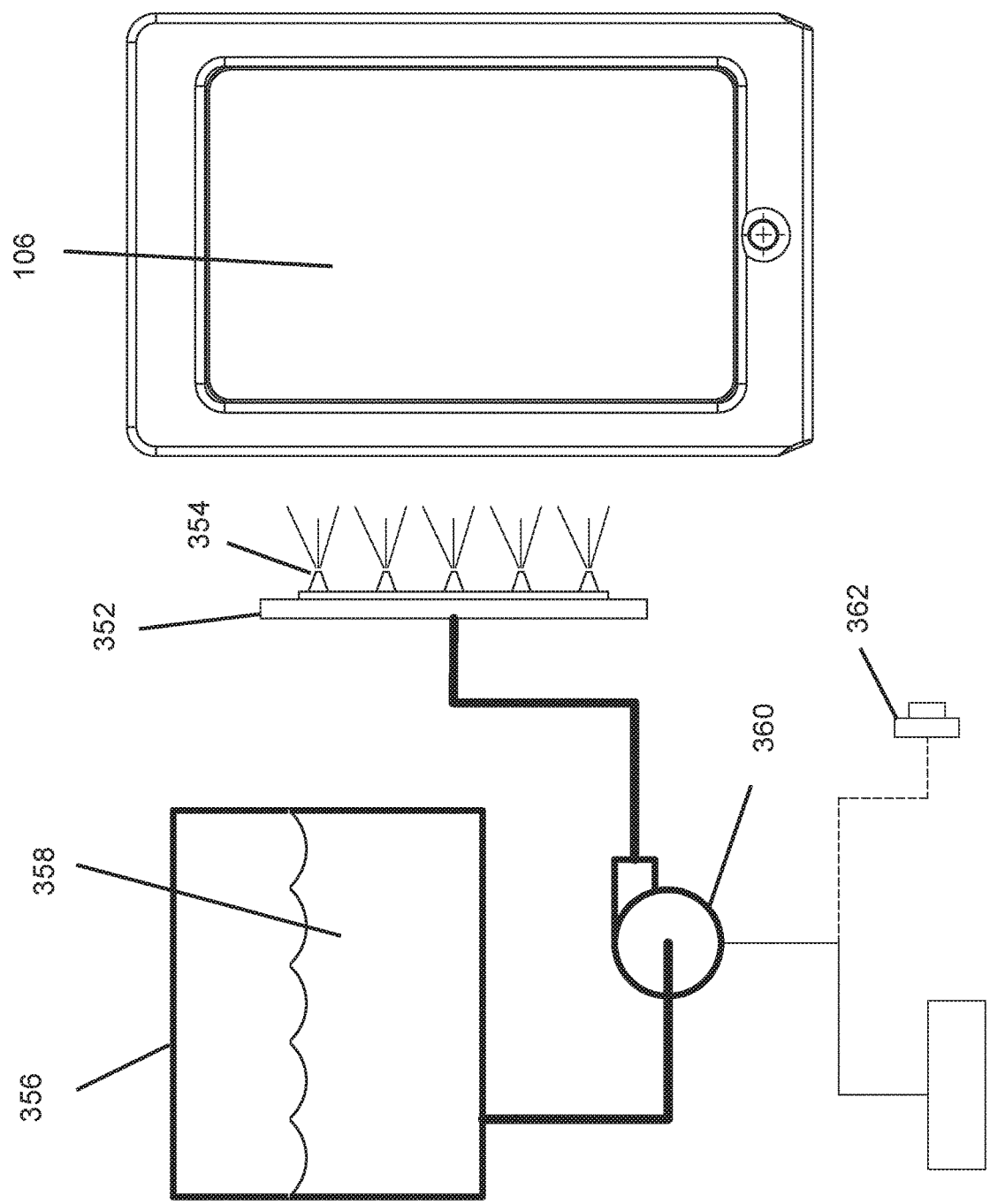
FIG. 40 is a schematic view of one embodiment of the present invention.

FIGS. 39 and 40 show a spray unit 352 with nozzles 354. The spray unit 352 disperses a sanitizing spray on the electronic device 106. The spray unit is oriented in the same direction as insertion of the electronic device 106. The nozzles 354 spray the sanitizing spray on the electronic device 106. Spray unit 352 is aligned with a charging aperture 122. A second spray unit 356 is aligned with another charging aperture. The separate spray units 352, 356 spray each electronic device 106 to sanitize devices installed within the charging apertures of the base. In one embodiment, a separate spray unit is installed for each charging aperture to allow for coverage of each electronic device 106.

FIG. 40 shows a reservoir 356 for the sanitizing spray 358, such as a liquid or gel. Pump 360 sprays the sanitizing spray 358 through the nozzles 354 of spray unit 352 onto the electronic device 106. Reservoir 356 may supply the spray to each unit 352, 356 or a single unit. Pump 360 is powered by a power source 362.

Figure 41:
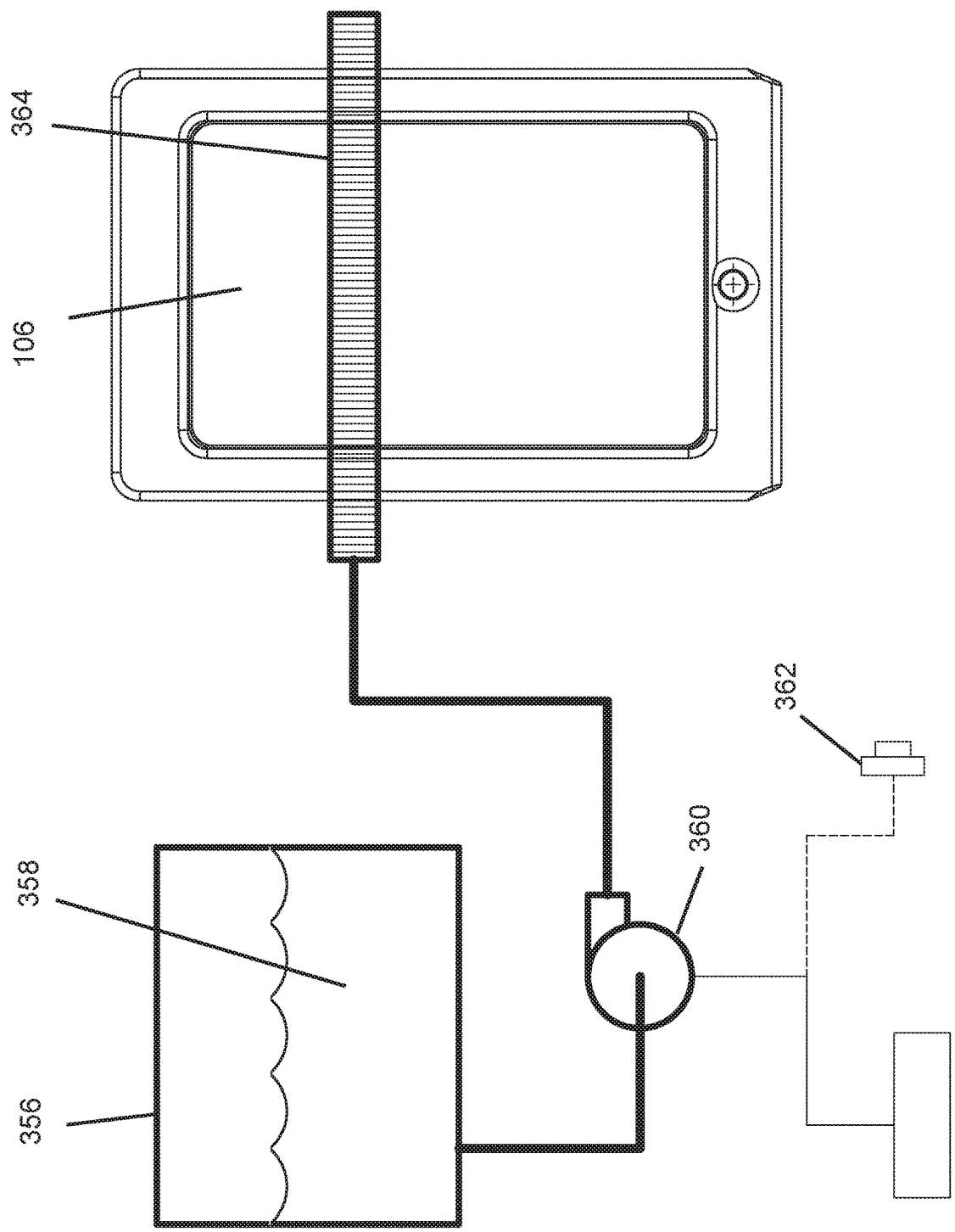
FIG. 41 is a schematic view of one embodiment of the present invention.

FIG. 41 shows a reservoir 356 for the sanitizing spray 358, such as a liquid or gel. Pump 360 sprays the sanitizing spray 358 through the brush 364 associated with the charging aperture. The brush of one embodiment may include a wick that supplies the sanitizing spray to the brush. In one embodiment, a brush is installed within each charging aperture 122. The brush 364 applies the sanitizing spray 358 to the electronic device 106 and brushes the spray 358 across the device 106. Reservoir 356 may supply the spray to each brush 364 or a single brush. Pump 360 is powered by a power source 362.

Figure 42:
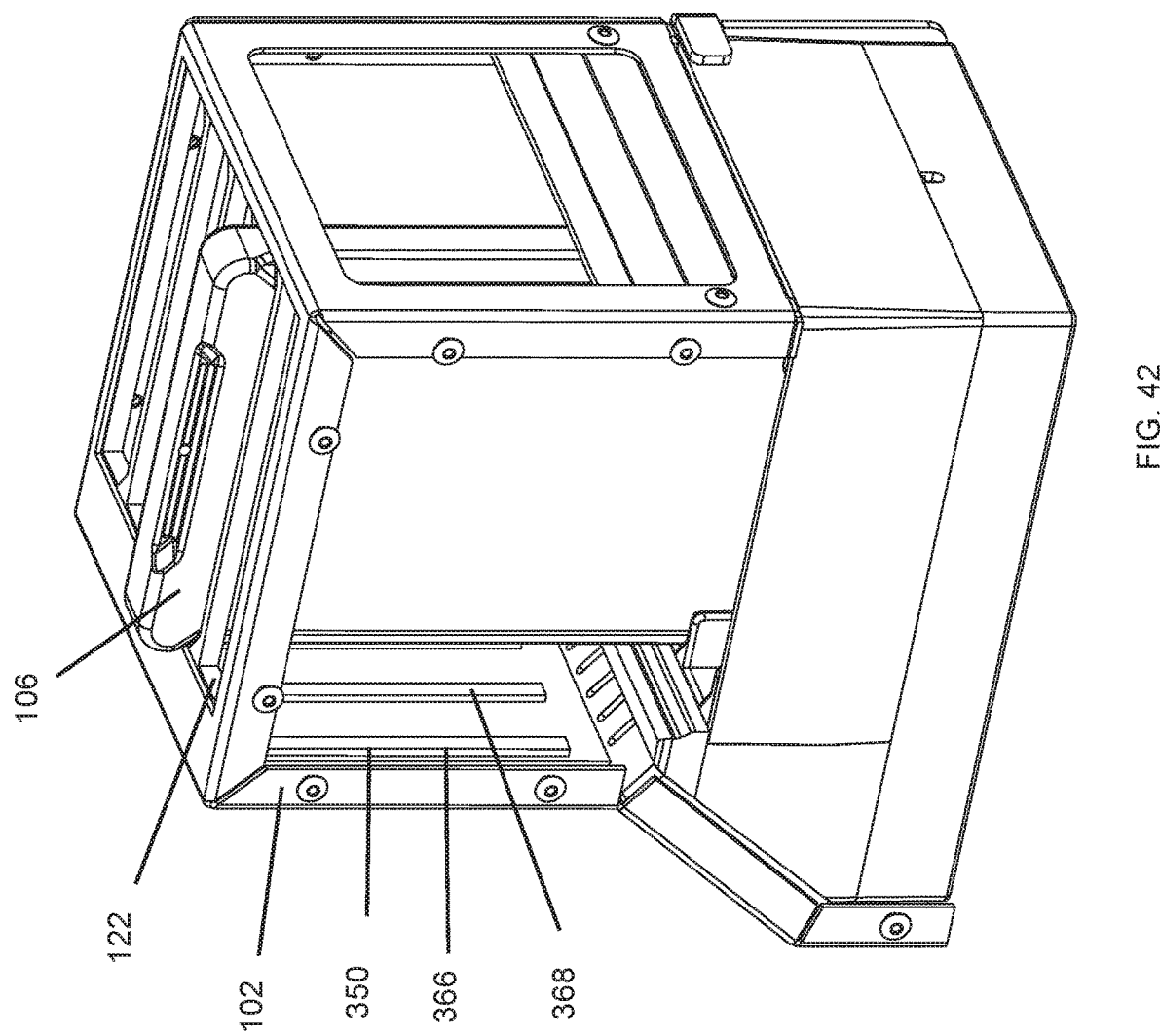
FIG. 42 is a perspective view of one embodiment of the present invention.

FIG. 42 shows another embodiment of the sanitizing system 350. The sanitizing system 350 shown in FIG. 42 implements lights 366, 368 that sanitize the electronic device 106. Each light 366, 368 is associated with a charging aperture 122. The lights 366, 368 are oriented to align with the charging aperture 122 with insertion of the electronic device 102. The lights may be ultraviolet lights or other lights that disinfect the electronic device 102. Applying the light for a particular amount of time disinfects and/or sanitizes the electronic device 102.

The server may control the sanitizing system 350. The server may track sanitation of each device. In another embodiment, the base controls the sanitizing system. The system of one embodiment maintains records indicating that devices have been sanitized and the time of sanitizing the devices. In one embodiment, the system activates an alert if the light or spray system is not functioning due to power failure, bad pump, no sanitizing spray, or non-functioning light. The server may maintain records of when the devices 106 were sanitized. The server may also activate an alert for when the sanitizing systems are not functioning properly.

The sanitizing systems may sanitize all charging apertures regardless or may only sanitize those charging apertures occupied by a device. The sanitizing system tracks the device identifier and sanitization records to confirm the sanitation of the devices.

The rules logic system, such as the server, of one embodiment may require sanitation of the device 106 before releasing the device. The system may lock the device until the device has been sanitized. The system may sanitize the device and release the device or release another device that has been sanitized to the user.

From the foregoing, it will be seen that the present invention is one well adapted to obtain all the ends and objects herein set forth, together with other advantages which are inherent to the structure.

It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

What is claimed is:

1. A base system for securing a mobile device stored within a base wherein the mobile device is associated with a unique device identifier, wherein the base releases the device to an authenticated user, the system comprising:
   said base that accepts at least a portion of the mobile computing device wherein the base restricts access to the mobile computing device;
   a lock that secures the device within the base when locked and the lock releases the device from the base when unlocked;
   an identification system that identities the device identifier of the mobile computing device inserted into the base;
   an authentication system that identifies the authenticated user;
   a rules logic system that applies rules to the authenticated user, wherein the rules logic system applies at least one rule, the rules logic system transmitting an unlock message to the base instructing the base to unlock the device if the rule is met;
   wherein the rule is based upon the authenticated user;
   the lock releasing the device from the base after receiving the unlock message;
   wherein the rules logic system restricts access to the device if the authenticated user has not returned a previously released device to the base, the rules logic system transmitting the unlock message to the base if an allowed number of devices have been released to the user, the rules logic system denying access if the user has exceeded the allowed number.

2. A base system for securing a mobile device stored within a base, wherein the mobile device is associated with a unique device identifier, wherein the base releases the device to an authenticated user, the system comprising:
   said base that accepts at least a portion of the mobile computing device, wherein the base restricts access to the mobile computing device;
   a lock that secures the device within the base when locked and the lock releases the device from the base when unlocked;
   an identification system that identities the device identifier of the mobile computing device inserted into the base;
   an authentication system that identifies the authenticated user;
   a rules logic system that applies rules to the authenticated user, wherein the rules logic system applies at least one rule, the rules logic system transmitting an unlock message to the base instructing the base to unlock the device if the rule is met;
   wherein the rule is based upon the authenticated user;
   the lock releasing the device from the base after receiving the unlock message;
   wherein the rules logic system restricts access to the device if the base has released a device to the authenticated user within a defined wait period, the rules logic system transmitting the unlock message to the base if the wait period has passed, the rules logic system denying access to the authenticated user if the wait period has not passed.

3. A base system for securing a mobile device stored within a base, wherein the mobile device is associated with a unique device identifier, wherein the base releases the device to an authenticated user, the system comprising:
   said base that accepts at least a portion of the mobile computing device, wherein the base restricts access to the mobile computing device;
   a lock that secures the device within the base when locked and the lock releases the device from the base when unlocked;
   a server in communication with the base, wherein the server authenticates the authenticated user prior to unlocking a device for removal from the base, the server transmitting an unlock message to the base instructing the base to unlock the device;
   the lock releasing the device from the base after receiving the unlock message;
   wherein the server identifies a mobile electronic device that has not been returned to the base within a predefined time period, wherein the server generates an alert that the mobile electronic device has not been returned to the base within the predefined time period.

4. The system of claim 3, wherein the server sends the mobile electronic device a deactivation instruction to deactivate upon the server determining the device has not been returned to the base within the predefined time period, wherein the device deactivates upon receiving the deactivation instruction from the server.

5. A base system for securing a mobile device stored within a base wherein the mobile device is associated with a unique device identifier, wherein the base releases the device to an authenticated user, the system comprising:

said base that accepts at least a portion of the mobile computing device wherein the base restricts access to the mobile computing device;

a sanitizing system coupled to the base, wherein the sanitizing system sanitizes the mobile computing device installed within the base;

a server in communication with the base wherein the server transmits an unlock message to the base instructing the base to unlock the device;

the lock releasing the device from the base after receiving the unlock message;

wherein the server transmits the unlock message if the sanitizing system has sanitized the mobile computing device since the mobile computing device has been returned to the base and prior to releasing the mobile computing device.

6. A base system for securing a mobile device stored within a base wherein the mobile device is associated with a unique device identifier, wherein the base releases the device to an authenticated user, the system comprising:

said base that accepts at least a portion of the mobile computing device wherein the base restricts access to the mobile computing device;

a sanitizing system coupled to the base, wherein the sanitizing system sanitizes the mobile computing device installed within the base;

a server in communication with the base wherein the server transmits an unlock message to the base instructing the base to unlock the device;

the lock releasing the device from the base after receiving the unlock message;

a sanitizing brush installed within the base that contacts the mobile computing device as the mobile computing device is inserted into the base.

\* \* \* \* \*